United States Patent [19]
Akagi et al.

[11] Patent Number: 5,635,500
[45] Date of Patent: Jun. 3, 1997

[54] CEPHEM COMPOUND AND PHARMACEUTICAL COMPOSITION CONTAINING THE COMPOUND

[75] Inventors: Hiroshi Akagi; Masaru Yasui; Yoshifumi Hara; Hideaki Hanaki; Akio Hyodo, all of Tokushima, Japan

[73] Assignees: Otsuka Kagaku Kabushiki Kaisha, Osaka; Taiho Pharmaceutical Co., Ltd., Tokyo, both of Japan

[21] Appl. No.: 240,663

[22] PCT Filed: Sep. 16, 1993

[86] PCT No.: PCT/JP93/01326

§ 371 Date: May 16, 1994

§ 102(e) Date: May 16, 1994

[87] PCT Pub. No.: WO94/06804

PCT Pub. Date: Mar. 31, 1994

[30] Foreign Application Priority Data

Sep. 18, 1992 [JP] Japan ................................ 4-249279

[51] Int. Cl.$^6$ .................. C07D 501/24; A61K 31/545
[52] U.S. Cl. ................................. 514/203; 540/225
[58] Field of Search ............................ 540/225, 227; 514/203

[56] References Cited

U.S. PATENT DOCUMENTS

| | | |
|---|---|---|
| 4,307,116 | 12/1981 | Farge et al. ................. 540/227 |
| 4,584,290 | 4/1986 | Takaya et al. ............... 514/206 |

*Primary Examiner*—John M. Ford
*Attorney, Agent, or Firm*—Armstrong, Westerman, Hattori, McLeland & Naughton

[57] ABSTRACT

The object of the present invention is to provide a cephem compound having high activity against various pathogenic microorganisms. The cephem compound of this invention is represented by the general formula

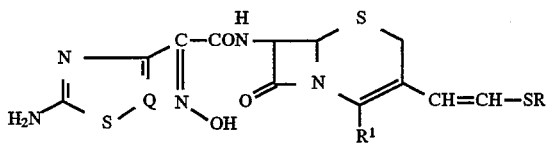

wherein Q represents CH or N; $R^1$ represents a carboxylate etc; and R represents

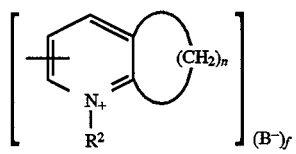

or the group

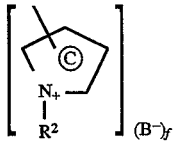

where $R^2$ represents a lower alkyl group etc, n represents an integer of 0 or 1 through 3, $B^-$ represents an anion, f is equal to 0 when $R^1$ represents a carboxylate and 1 where $R^1$ represents a carboxyl group, and the ring C represents a 5-membered heterocyclic group of not more than 4 nitrogen atoms, which may be substituted by lower alkyls.

4 Claims, No Drawings

CEPHEM COMPOUND AND PHARMACEUTICAL COMPOSITION CONTAINING THE COMPOUND

This application is a 371 of PCT/JP93/01326 filed Sep. 16, 1993.

TECHNICAL FIELD

This invention relates to a novel cephem compound, a process for producing the compound and a pharmaceutical composition comprising the same.

PRIOR ART

With the spreading use of third-generation cephalosporins in recent years, infectious diseases associated with meticillin-resistant *Staphylococcus aureus* (MRSA) are presenting serious problems. These cephalosporins of the third generation have potent activity against gram-negative bacilli but because of their relatively low activity against gram-positive cocci, the strains of *S. aureaus* which are resistant to β-lactam antibiotics have increased in number and the resultant refractory infections constitute a serious threat today. The only therapeutic drug available for MRSA infections today is vancomycin which is a polypeptide antibiotic but since it has side effects such as eczema and renal toxicity, vancomycin calls for caution in administration.

As 3-thiovinylcephalosporin derivatives having antimicrobial activity, the compounds described in Japanese Examined Patent Application 17592/1987 and Japanese Patent Unexamined Application 130292/1984 (EP-A111281) gazettes are known to this day. The latter gazette describes compounds having an alkoxyimino group in the side chain in the 7-position and a thiovinyl quaternary ammonium salt in the. 3-position of the cephalosporin nucleus but does not refer to a hydroxyimino group. Furthermore, there is no disclosure in these prior art publications that a 3-thiovinylcephalosporin derivative is active against MRSA.

Disclosure of Invention

It is an object of this invention to provide cephem compounds having excellent antimicrobial activity and, in particular, novel cephem compounds which are active against MRSA and safe to use.

It is another object of the invention to provide a process for producing the above-mentioned compounds.

A further object of this invention is to provide a pharmaceutical composition for the therapy of MRSA-induced infectious diseases.

For the purpose of accomplishing the above-mentioned objects, the inventors of this invention synthesized and screened a variety of cephem compounds and discovered that a cephem compound having a thiovinyl quaternary ammonium salt in the 3-position and a hydroxyimino group in the side chain moiety in the 7-position of the cephalosporin nucleus has excellent antimicrobial activity and is particularly active against MRSA. This invention has been developed on the basis of the above discovery.

The cephem compound of this invention is a novel compound of the following general formula (1)

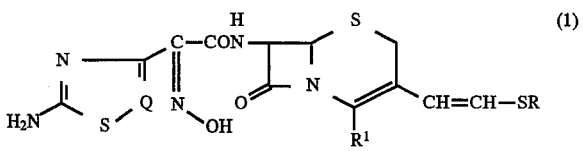

[wherein Q represents CH or N, $R^1$ represents a carboxylate or a carboxyl group, and R represents the group

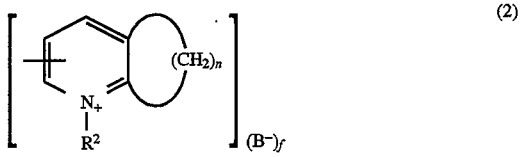

or the group

where $R^2$ represents a lower alkyl group, a lower alkenyl group, a lower alkynyl group, a hydroxy(lower)alkyl group or the group —A—CO—$R^3$ (where A represents a $C_{1-6}$ alkylene group, a phenylene group, a benzylene group or a xylylene group, $R^3$ represents a hydroxyl group, a lower alkyl group, a phenyl group which may be substituted by hydroxyl, an amino group, a lower alkylamino group or an amino acid amino group), n represents an integer of 0 or 1 through 3, $B^-$ represents an anion, f is equal to 0 when $^-R^1$ represents a carboxylate and 1 when $R^1$ represents a carboxyl group, and the ring C represents a 5-membered heterocyclic group of not more than 4 nitrogen atoms, which may be substituted by lower alkyl].

The respective groups mentioned in this specification specifically mean the following.

The lower alkyl group includes $C_{1-6}$ alkyl groups, such as methyl, ethyl, propyl, isopropyl, butyl, isobutyl, tert-butyl, pentyl and hexyl, among others.

The lower alkenyl group includes $C_{2-6}$ alkenyl groups, such as vinyl, allyl, crotyl, 2-pentenyl and 2-hexenyl, among others.

The lower alkynyl group includes $C_{2-6}$ alkynyl groups, such as ethynyl, 1-propynyl, 2-propynyl, 2-butynyl, 1-methyl-2-propynyl, 2-pentynyl and 2-hexynyl, among others.

The hydroxy(lower)alkyl group includes hydroxy alkyl groups having 1–6 carbon atoms in the alkyl moiety, such as hydroxymethyl, 2-hydroxyethyl, 3-hydroxypropyl, 4-hydroxybutyl, 5-hydroxypentyl and 6hydroxyhexyl, among others.

The $C_{1-6}$ alkylene group includes methylene, ethylene, 1-methylethylene, propylene, 2-ethylpropylene, butylene, pentylene and hexylene, among others.

The phenyl group which may be substituted by hydroxyl includes phenyl and phenyl groups substituted by 1–3 hydroxyl groups, such as o-hydroxyphenyl, p-hydroxyphenyl, m-hydroxyphenyl, 2,4-dihydroxyphenyl, 3,4dihydroxyphenyl and 3,4,5-trihydroxyphenyl, among others.

The lower alkylamino group includes $C_{1-6}$ monoalkylamino groups such as methylamino, ethylamino, propylamino, butylamino, hexylamino, etc. and $C_{2-12}$ dialkylamino groups such as dimethylamino, diethylamino, dipropylamino, dibutylamino, dihexylamino and so on.

The amino acid amino group means the residue available on elimination of one hydrogen atom from the amino group of an amino acid. The amino acid mentioned above includes α-amino and β-amino acids of 3–10 carbon atoms, such as alanine, isoleucine, glycine, serine, threonine, valine, norvaline, isovaline, norleucine, leucine and methionine, among others.

The ring represented by C is a 5-membered heterocyclic group comprising not more than 4 nitrogen atoms, which may be substituted by lower alkyl, thus including oxazole, thiazole, isoxazole, isothiazole, oxathiazole, thiadiazole, oxathiadiazole, pyrazole, imidazole, triazole, oxatriazole, thiatriazole, tetrazole, etc., which may respectively be substituted by one lower alkyl group on a ring nitrogen or carbon atom. Such heterocyclic rings can be specifically represented by the following structural formulas.

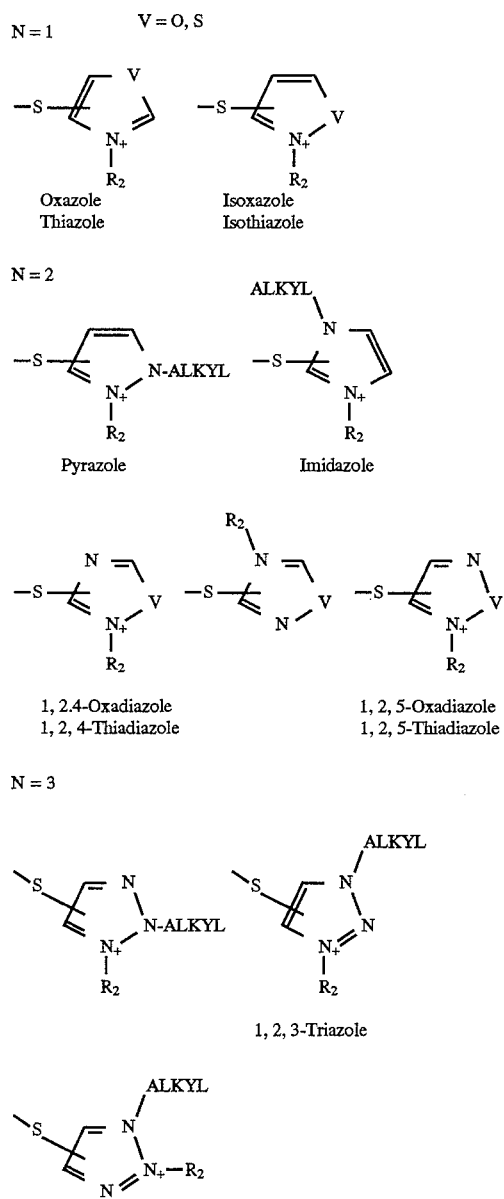

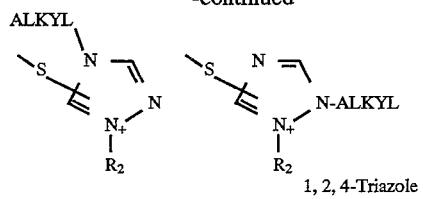

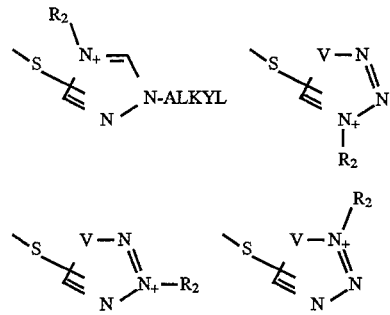

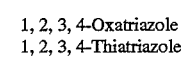

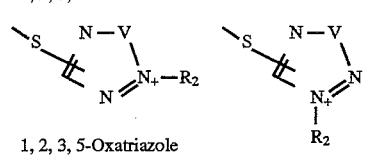

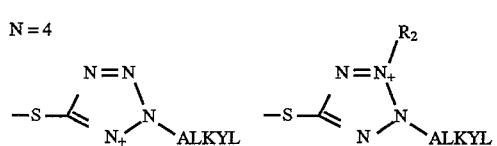

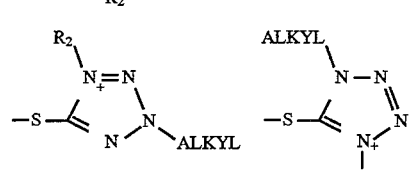

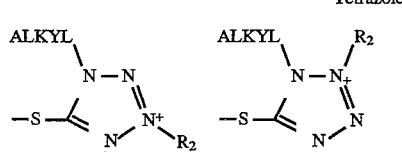

The anion represented by B⁻ includes the acid residues of various inorganic acids such as hydrochloric acid, hydrobromic acid, nitric acid, sulfuric acid, perchloric acid, etc. and of various organic acids such as methanesulfonic acid, ethanesulfonic acid, 2-chloroethanesulfonic acid, benzenesulfonic acid, p-toluenesulfonic acid, p-ethylsulfonic acid, p-chlorosulfonic acid, naphthalenesulfonic acid, trifluoroacetic acid, formic acid, etc.

The cephemcarboxy-protecting group includes those protective ester residues which are conventionally used in the synthesis of cephem compounds as well as pharmacologically acceptable protective ester residues. The protective ester residues conventionally used in cephem synthesis are those ester residues which are indifferent to various chemical modifications of β-lactum compounds but can be easily cleaved off in the conversion to the pharmacologically acceptable protective ester residues which are described below. The pharmacologically acceptable protective ester residues are nontoxic ester residues which are readily cleaved off by hydrolysis in vivo and, as such, rapidly cleaved off in the human blood and tissues. Such esters may be those known esters which are commonly used in the field of antibiotics, thus including but being not limited to the ester residues described in Japanese Patent Application Kokai S-49-81380 and H. E. Flynn (ed.): Cephalosporins and Penicillins, Chemistry and Biology (1972, Academic Press). As the preferred species may be mentioned $C_{1-18}$ alkyl groups such as methyl, ethyl, propyl, butyl, tertbutyl, 1,1-dimethylpropyl, 1-cyclopropylmethyl, pentyl, hexyl, decyl, undecyl, dodecyl, tetradecyl, hexadecyl, octadecyl, etc.; halo(lower)alkyl groups substituted by 1–3 chlorine, bromine or iodine atoms, such as iododecyl, chloromethyl, 2,2-dibromoethyl, 2,2,2-trichloroethyl, 2,2,2-tribromoethyl, etc.; methyl substituted by 1–3 phenyl groups which may be substituted by nitro or alkoxy, such as benzyl, diphenylmethyl, trityl, p-nitrobenzyl, o-methoxybenzyl, p-methoxybenzyl, di(p-methoxyphenyl)methyl, etc., lower alkoxymethyl groups such as methoxymethyl, ethoxymethyl, n-propyloxymethyl, isopropyloxymethyl, n-butoxymethyl, isobutoxymethyl, etc.; (lower) alkylcarbonyloxy(lower)alkyl groups such as acetoxymethyl, acetoxyethyl, propionyloxyethyl, n-butyryloxymethyl, isobutyryloxymethyl, pivaloyloxymethyl, 1-acetoxyethyl, pivaloyloxyethyl, pivaloyloxypropyl, 1-propionyloxybutyl, etc.; $C_{5-7}$ cycloalkylcarbonyloxy-lower alkyl groups such as cyclopentylcarbonyloxymethyl, cyclohexylcarbonyloxymethyl, etc.; benzylcarbonyloxy (lower)alkyl groups such as benzylcarbonyloxymethyl etc.; benzoyloxy(lower)alkyl groups such as benzoyloxymethyl, benzoyloxyethyl, etc.; lower alkoxycarbonyloxy(lower) alkyl groups such as methoxycarbonyloxymethyl, 1-ethoxycarbonyloxyethyl, 3-methoxycarbonyloxypropyl, etc.; benzyloxy(lower)alkyl groups such as benzyloxymethyl, benzyloxyethyl, etc.; and such other groups as.2-cyano-1,1-dimethylethyl, bromobenzoylmethyl, p-nitrobenzoylmethyl, dimethylaminomethyl, methylthiomethyl, phenylthiomethyl, succinimidomethyl, 1,1-dimethyl-2propenyl, 1,3-dimethyl-3-butenyl, 3-phthalidyl, crotonolacton-4-yl, γ-buyrolacton-4-yl, tetrahydropyranyl, dimethylaminoethyl, dimethylchlorosilyl, trichlorosilyl, (2-oxo-1,3-dioxoden-4-yl)methyl, (5-methyl-2-oxo-1,3-dioxoden-4-yl)methyl, (5-phenyl-2-oxo-1,3-dioxoden-4yl)methyl, pyridine-1-oxide-2-methyl and quinoline-1-oxide-2-methyl, among others.

The nontoxic salt of the compound of general formula (1) includes medicinally acceptable salts such as hydrochloride, hydrobromide, hydroiodide, sulfate, etc., salts with organic carboxylic acids, such as citrate, maleate, lactate, tartrate, etc., salts with organic sulfonic acids such as methanesulfonate, hydroxymethanesulfonate, aminoethanesulfonate, benzenesulfonate, toluenesulfonate, etc., salts with amino acids, such as arginine salt, lysine salt, serine salt, aspartate, glutamate, aminoacetate, etc., alkali metal salts such as sodium salt, potassium salt, lithium salt, etc. and alkaline earth metal salts such as calcium salt, magnesium salt, etc.

The preferred species of said compound of general formula (1) and said nontoxic salt thereof are as follows: 7-[2-hydroxyimino-2-(2-aminothiazol-4-yl)acetamido]-3-[2-(1-carbamoylmethyl-4-pyridinio)thiovinyl]-3-cephem-4-carboxylate or its salt, 7-[2-hydroxyimino-2-(2-aminothiazol-4-yl)acetamido]-3-[2-(1-ethyl-4pyridinio) thiovinyl]-3-cephem-4-carboxylate or its salt, 7-[2-hydroxyimino-2-(2-aminothiazol-4-yl)acetamido]-3-{2-[1-(2-hydroxyethyl)-4-pyridinio]thiovinyl}-3-cephem-4-carboxylate or its salt, 7-[2-hydroxyimino-2-(2-aminothiazol-4-yl)acetamido]-3-[2-(1-carboxymethyl-4-pyridinio)thiovinyl]-3-cephem-4-carboxylate or its salt, 7-[2-hydroxyimino-2-(2-aminothiazol-4-yl)acetamido]-3-[2-(1-acetonyl-4-pyridinio)-thiovinyl]-3-cephem-4-carboxylate or its salt, 7-[2-hydroxyimino-2-(2-aminothiazol-4-yl)acetamido]-3-[2-(1-methyl-2-pyridinio) thiovinyl]-3-cephem-4-carboxylate or its salt, 7-[2-hydroxyimino-2-(2-aminothiazol-4-yl)acetamido]-3-{2-[1-(4-carboxybenzyl)-4-pyrydinio]thiovinyl}-3-cephem-4-carboxylate or its salt, 7-[2-hydroxyimino-2-(2-aminothiazol-4-yl)acetamido]-3-{2-[1-(N,N-diethylaminocarbonylmethyl)-4-pyridinio]thiovinyl}-3-cephem-4-carboxylate or its salt, 7-[2-hydroxyimino-2-(2-aminothiazol-4-yl)acetamido]-3-[2-(1-allyl-4-pyridinio) thiovinyl]-3-cephem-4-carboxylate or its salt, 7-[2-hydroxyimino-2-(2-aminothiazol-4-yl)acetamido]-3-[2-(1,4-dimethyl-1,2,4-triazolio-5-yl)thiovinyl]-3-cephem-4carboxylate or its salt, 7-[2-hydroxyimino-2-(2-aminothiazol-4-yl)acetamido]-3-[2-(1,3-dimethylimidazolio-2-yl)thiovinyl]-3-cephem-4-carboxylate or its salt, and 7-[2-hydroxyimino-2-(2-aminothiazol-4-yl)acetamido]-3-[2-(1,3-dimethyl-1,2,3-triazolio-5-yl)thiovinyl]-3-cephem-4-carboxylate or its salt.

The compound (1) of this invention and its starting compounds include cis- and trans-isomers and mixtures of such cis- and trans-isomers.

In the case of compound (1), the cis.-isomer, for instance, means one of the geometrical isomers having the partial structure of the following general formula (4) and the trans-isomer means the other geometrical isomer having the partial structure of the following formula (5).

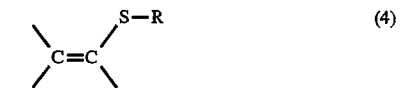 (4)

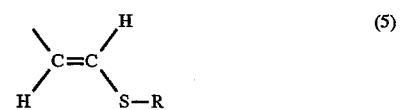 (5)

While the compound (1) and salt thereof can be produced by various processes, the preferred is the process I described below.

Process-I

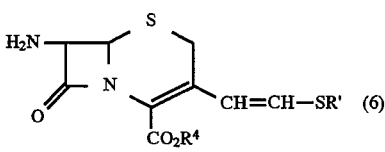 (6)

1) 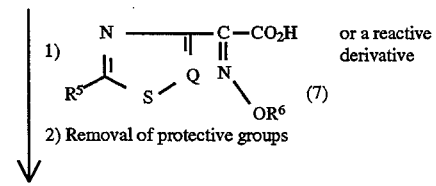 or a reactive derivative (7)

2) Removal of protective groups

-continued
Process-I

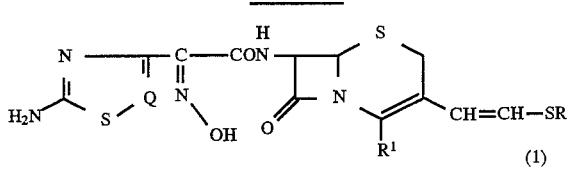

[wherein R⁴ represents a cephemcarboxy-protective group; R' represents the group

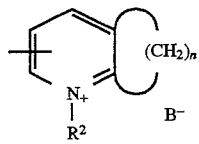

or the group

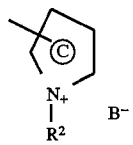

where $R^2$, n, $B^-$ and C are as defined hereinbefore; $R^5$ represents an amino group or a protected amino group; $R^6$ represents an oxime-protective group; and Q, R and $R^1$ are as defined hereinbefore]

According to the above process I, a compound of general formula (1) can be produced by subjecting an amine compound of general formula (6) and a carboxylic acid compound of general formula (7) or a reactive derivative thereof, as derived by activating its carboxyl group, to the conventional amide bond-forming reaction and removing the protective groups from the resultant product.

The carboxy-protective group designated by $R^4$ here includes those carboxy-protective groups which are conventionally used in this field and can be easily cleaved off, e.g. tri(lower)alkylsilyl groups such as trimethylsilyl etc., benzhydryl, p-methoxybenzyl, tert-butyl, p-nitrobenzyl and phenacyl, among others.

The protective group of the protected amino group $R^5$ includes a broad range of protective groups which can be easily eliminated under mild conditions, e.g. tri(lower) alkylsilyl groups such as trimethylsilyl etc., acyl-type protective groups such as formyl, trifluoroacetyl, acetyl, tert-butylcarbonyl, methoxyacetyl, benzyloxycarbonyl, p-nitrobenzyloxycarbonyl, etc., and aralkyl-type protective groups such as benzyl, benzhydryl, trityl and so on.

The oxime-protective group $R^6$ includes those protective groups which can be easily eliminated under mild conditions and are conventionally employed in this field, such as trityl, tetrahydropyranyl and so on.

The reaction between compound (6) and compound (7) or a reactive derivative of the latter can be carried out under conditions similar to those of known amide bond-forming reactions.

The reactive derivative of compound (7) includes but is not limited to the acid halides such as acid chloride, acid bromide, etc., mixed acid anhydrides with various acids such as substituted phosphoric acids, dialkyl phosphites, sulfurous acid, thiosulfuric acid, monoalkyl carbonate, organic carboxylic acids, etc., symmetric acid anhydride, active acid amides with imidazole, dimethylpyrazole, etc., and active esters such as the p-nitrophenyl ester, phenylthioester, carboxymethylthioester, etc. or esters with N-hydroxy compounds such as N-hydroxypiperidine, N-hydroxysuccinimide, N-hydroxyphthalimide and so on.

When this invention is practiced using compound (7) in the form of a free carboxylic acid, it is preferable to use a condensing agent such as N,N-diethylcarbodiimide, N,N-dicyclohexylcarbodiimide or the like.

The solvent that can be used in the above reaction may be virtually any solvent that does not take part in the reaction and the reaction is generally carried out under cooling or in the neighborhood of room temperature. The solvent mentioned above includes ethers such as diethyl ether, tetrahydrofuran, dioxane, etc., halogenated hydrocarbons such as dichloromethane, dichloroethane, chloroform, carbon tetrachloride, etc., aromatic hydrocarbons such as benzene, toluene, etc., amines such as pyridine, piperidine, triethylamine, etc., esters such as ethyl acetate, ethyl formate, etc., aprotic polar solvents such as dimethylformamide, hexamethylphosphoric triamide, dimethyl sulfoxide, etc., and acetone, among others, and mixtures of such solvents.

Depending on the reactive derivative of the carboxylic acid, the reaction may be preferably conducted in the presence of a basic compound. The basic compound includes organic bases, e.g. trialkylamines such as triethylamine, tributylamine, etc., pyridine, picoline, 1,8-diazabicyclo[5.4.0]undecene-7, etc. and inorganic bases, e.g. sodium hydrogen carbonate, potassium hydrogen carbonate, sodium carbonate, potassium carbonate, sodium hydroxide, potassium hydroxide and so on.

The amount of said carboxylic acid compound of general formula (7) or a reactive derivative thereof relative to the amine compound of general formula (6) for use in this reaction is generally about 1–10 mol equivalents and preferably about 1–3 mol equivalents. The amount of said basic compound relative to the amine compound of general formula (6) is generally about 1–30 mol equivalents and preferably about 2–10 mol equivalents. The reaction time is generally about 1–24 hours and preferably about 1–6 hours.

Removal of protective groups from the amide bonding product thus obtained can be carried out as follows. For example, when the protective group is a tri(lower)alkylsilyl group, it can be removed with water. When the protective group is benzhydryl, trityl, p-methoxybenzyl, tert-butyl or formyl, for instance, it can be removed with formic acid, hydrochloric acid, trifluoroacetic acid, anisole-trifluoroacetic acid, acetic acid, phenol, cresol or the like. After the reaction, the compound of general formula (I) according to this invention can be isolated and purified by column chromatography using a hyperporous polymer such as Diaion HP-20, HP-21, SP-207 or CHP-20P (Mitsubishi Kasei Corporation), Amberlite XAD-2 (Rhom & Haas Co.) or the like.

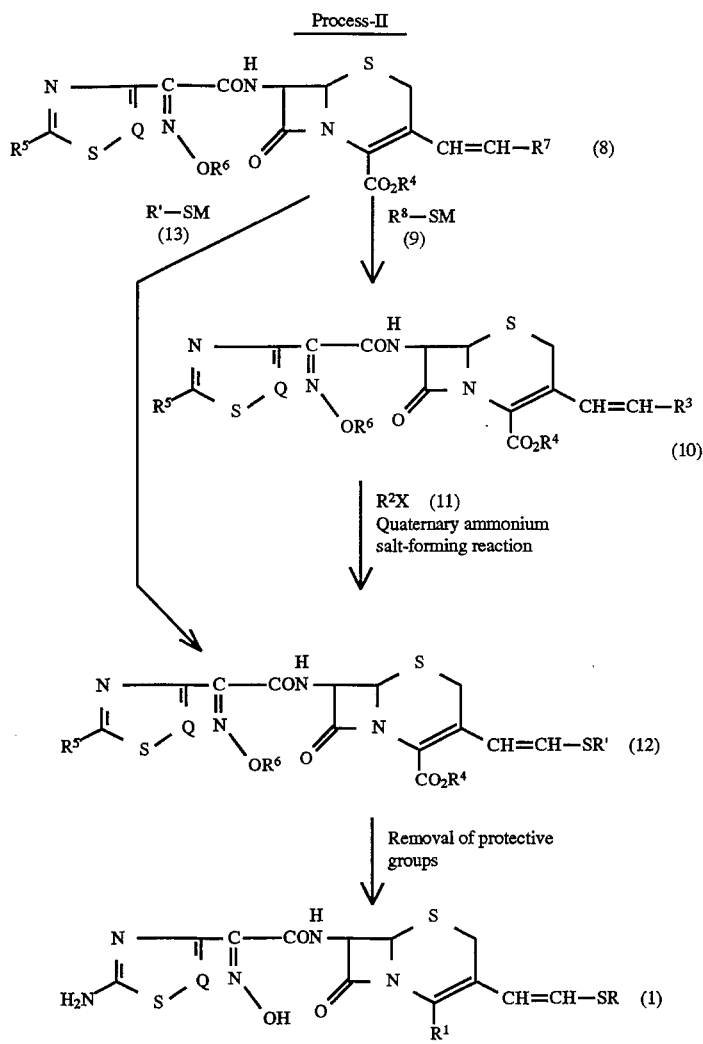

[wherein Q, R, $R^1$, $R^4$, $R^5$, $R^6$ and R' are as defined hereinbefore; $R^7$ represents a halogen atom, a lower acyloxy group or a sulfonyloxy group; $R^8$ represents the group

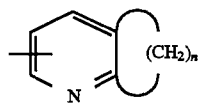

or the group

where C and n are as defined hereinbefore; X represents a halogen atom; and M represents a hydrogen atom or a metal atom]

Referring to the above production process II, the compound of general formula (1) according to this invention can be obtained by reacting a cephalosporin compound of general formula (8) or a salt thereof with a mercapto compound of general formula (9), then reacting the resultant compound of general formula (10) with a halogenated organic compound of general formula (11) and removing the protective groups from the resultant compound of general formula (12). The compound of general formula (12) can also be obtained in one step by reacting a compound of general formula (8) with a quaternized mercapto compound of general formula (13).

The reaction between compound (8) and compound (9) is generally carried out in an organic solvent or a mixture of a hydrophilic organic solvent with water, such as ketones such as acetone etc., halogenated hydrocarbons such as chloroform, dichloromethane, dichloroethane, etc., ethers such as diethyl ether, tetrahydrofuran, dioxane, etc., acetonitrile, alcohols such as methanol, ethanol, etc., dimethyl sulfoxide, dimethylformamide, water, phosphate buffers, etc. To hasten the reaction, a base or a salt may be added to the reaction system. As examples of said base or salt may be reckoned inorganic bases such as sodium hydroxide, potassium hydroxide, sodium carbonate, potassium carbonate, etc. and organic amines, e.g. trialkylamines such as triethylamine, diisopropylamine, etc. As said salt, quaternary ammonium salts such as tetrabutylammonium salt can be mentioned by way of example. This reaction is generally carried out under cooling or around room temperature.

The halogenated organic compound of general formula (11) includes lower alkyl halides, lower alkenyl halides, lower alkinyl halides, hydroxy(lower) alkyl halides, carboxy (lower)alkyl halides, carbamoyl (lower)alkyl halides, and lower alkanoyl(lower)alkyl halides, among others. The halides may be chlorides, bromides and iodides, among others. The solvent which can be used for the reaction between compound (10) and compound (11) includes halogenated hydrocarbons such as dichloromethane, dichloroethane, chloroform, carbon tetrachloride, etc., aromatic hydrocarbons such as benzene, toluene, xylene, etc., ethers such as diethyl ether, tetrahydrofuran, dioxane, etc., and acetonitrile, among others. This reaction is conducted at room temperature—ca. 80° C., preferably at about 20°–50° C., and generally goes to completion in about 1–20 hours.

The reaction between compound (8) and compound (13) can be conducted under conditions similar to the conditions of the above-mentioned reaction between compound (8) and compound (9). The metal atom in general formulas (9) and (13) may for example be sodium, lithium, calcium, magnesium, silver or copper.

From the compound of general formula (12) thus obtained, the protective groups can be eliminated by the procedures described for Process I, whereby the compound of general formula (1) according to this invention is easily obtained.

The compound of this invention is formulated with suitable pharmaceutical carriers to provide a pharmaceutical composition in the per se known manner. As the carriers mentioned above, a variety of substances which are commonly used in pharmaceutical formulation, such as excipients, binders, disintegrators, lubricants, coloring agents, flavoring agents and other corrigents, surfactants, etc., can be mentioned.

There is no limitation on the dosage form in which the pharmaceutical composition of this invention can be administered for the treatment of infections, particularly infections caused by meticillin-resistant strains of *Staphyloccus aureus*, in man and other mammalian animals but a suitable dosage form can be chosen according to the objective of therapy. Thus, non-peroral dosage forms such as injections, suppositories, eyedrops, ointments, aerosols, etc., and peroral dosage forms such as tablets, coated tablets, powders, granules, capsules, solutions, pills, suspensions and emulsions can be mentioned.

The above-mentioned dosage forms are manufactured by the pharmaceutical procedures established in this field. Peroral dosage forms such as tablets, powders, granules, etc. can be manufactured by using, as said carriers, a variety of excipients such as lactose, sucrose, sodium chloride, glucose, urea, starch, calcium carbonate, kaolin, crystalline cellulose, silicic acid, methylcellulose, glycerin, sodium alginate, gum arabic, etc., binders such as simple syrup, glucose syrup, starch solution, gelatin solution, polyvinyl alcohol, polyvinyl ether, polyvinylpyrrolidone, carboxymethylcellulose, shellac, methylcellulose, ethylcellulose, water, ethanol, potassium phosphate, etc., disintegrators such as dried starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, lactose, etc., disintegration inhibitors such as sucrose, stearic acid, cacao butter, hydrogenated oil, etc., absorption promoters such as quaternary ammonium bases, sodium lauryl sulfate, etc., humectants such as glycerin, starch, etc., adsorbents such as starch, lactose, kaolin, bentonite, colloidal silica, etc. and lubricants such as purified talc, stearates, boric acid powder, polyethylene glycol, etc. If necessary, tablets may be coated or otherwise covered to provide dragees, gelatin-coated tablets, enteric tablets, film-coated tablets, double-layer tablets, multi-layer tablets and so on.

Pills can be manufactured by using, as carriers, various excipients such as glucose, lactose, starch, cacao butter, hydrogenated vegetable oil, kaolin, talc, etc., binders such as gum arabic powder, gum tragacanth powder, gelatin, etc. and disintegrators such as laminaran, agar and so on.

Capsules can be manufactured by blending the compound with various carriers such as those mentioned above and filling the resultant mixture into hard gelatin capsule shells or soft capsule shells.

Suppositories can be molded by using, as carriers, polyethylene glycol, cacao butter, lanolin, higher alcohols, higher alcohol esters, gelatin, semisynthetic glycerides, Witepsols (trademark of Dynamit Nobel), etc. together with suitable absorption promotors.

In processing the composition into injections, various diluents such as water, ethyl alcohol, macrogols, propylene glycol, ethoxylated isostearyl alcohol, polyoxylated isostearyl alcohol, polyoxyethylene-sorbitan fatty acid ester, etc., pH control agents and buffers such as sodium citrate, sodium acetate, sodium phosphate, etc., and stabilizers such as sodium pyrosulfite, ethylenediaminetetracetic acid, thioglycolic acid, thiolactic acid, etc. can be used as carriers. The pharmaceutical composition may contain sodium chloride, glucose or glycerin in a sufficient amount to make it isotonic. The conventional solubilizers, soothing agents, local anesthetics, etc. can also be incorporated. After addition of such carriers, a subcutaneous, intramuscular or intravenous injection can be manufactured by the per se known procedures.

The liquid composition may take such forms as aqueous or oil suspensions, solutions, syrups, elixirs and so on. These preparations can be manufactured using the conventional additives in the conventional manner.

The ointment, e.g. a paste, a cream or a gel, can be manufactured using a diluent such as white petrolatum, paraffin, glycerin, cellulose derivatives, polyethylene glycol, silicone, bentonite and so on.

The amount of the compound of this invention in the above-mentioned composition is dependent on dosage form, route of administration and therapeutic regimen and cannot, therefore, be stated in general terms. However, it can be liberally selected from a broad range. Generally speaking, the compound occurs in a proportion of about 1–70 weight %.

The route of administration of the composition is not limited to the parenteral, peroral, rectal, buccal and transdermal routes but can be selected according to dosage form, patient's age and sex and other background factors, degree or severity of illness and so on. For example, the tablets, pills, solutions, suspensions, emulsions, granules and capsules are administered perorally. The injections can be administered intravenously as they are or in admixture with infusions such as glucose, amino acid and other infusions or, if necessary, intramuscularly, intradermally, subcutaneously or intraperitoneally as they are. The suppositories are administered rectally. The ointments are applied to the skin or the oral mucosa, for instance.

The dosage of the compound of this invention can be selected according to the dosage form, patient's age and clinical condition, type of disease, and species of the compound. Generally speaking, about 100 mg to 10 g a day, or a larger dose, is administered to each patient. For the treatment of infectious diseases caused by pathogenic microorganisms, the daily average dose of about 50 mg, 100 mg, 250 mg, 1000 mg or 2000 mg can be administered.

To confirm the usefulness of the objective compound of this invention, the antibacterial activities of some representative species of the compound were determined by the agar plate dilution assay and the minimal inhibitory concentration (MIC) values against various bacteria were compared with those of FMOX (flomoxef). The results are shown in Table 1. Moreover, the $MIC_{80}$ values against clinically isolated meticillin-resistant and highly ciprofloxacin-resistant *Staphylococcus aureus* strains were compared with those of VCM (vancomycin), FMOX and CPFX (ciprofloxacin). The results are shown in Table 2. The test compounds were as follows.

Test compounds (a) 7-[2-Hydroxyimino-2-(2-aminothiazol-4-yl) acetamido]-3-[2-(1-carbamoylmethyl-4-pyridinio) thiovinyl]-3-cephem-4-carboxylate (syn-isomer)

(b) 7-[2-Hydroxyimino-2-(2-aminothiazol-4-yl) acetamido]-3-[2-(1-methyl-4-pyridinio)thiovinyl]-3-cephem-4-carboxylate (syn-isomer)

(c) 7-[2-Hydroxyimino-2-(2-aminothiazol-4-yl) acetamido]-3-{2-[1-(2-hydroxyethyl)-4-pyridinio) thiovinyl}-3-cephem-4-carboxylate (syn-isomer)

(d) 7-[2-Hydroxyimino-2-(2-aminothiazol-4-yl) acetamido]-3-[2-(1-carboxymethyl-4-pyridinio)thiovinyl-3-cephem-4-carboxylate (syn-isomer)

(e) Sodium 7-[2-hydroxyimino-2-(2-aminothiazol-4-yl) acetamido]-3-[2-(4-pyridyl)thiovinyl]-3-cephem-4-carboxylate (syn-isomer)

(f) 7-[2-Methoxyimino-2-(2-aminothiazol-4-yl) acetamido]-3-[2-(1-methyl-4-pyridino)thiovinyl]-3-cephem-4-carboxylate (syn-isomer)

TABLE 1

| Organism | Test compound | | | |
|---|---|---|---|---|
| | (a) | (b) | (c) | (d) |
| *S. aureus* FDA 209-P | 0.1 | 0.1 | 0.1 | 3.13 |
| *E. faecalis* ATCC-21212 | 0.2 | 0.2 | 0.2 | 12.5 |
| MRSA 92-1044 | 3.13 | 1.56 | 3.13 | 12.5 |
| *E. coli* NIHJ JC-2 | 0.0125 | 0.0125 | 0.125 | 0.0125 |
| *K. pneumoniae* NCTC-9632 | 0.025 | 0.025 | 0.025 | 0.025 |
| *S. marcescens* IFO-12648 | 0.1 | 0.05 | 0.05 | 0.05 |

| Organism | Test compound | | |
|---|---|---|---|
| | (e) | (f) | FMOX |
| *S. aureus* FDA 209-P | 0.1 | 0.39 | 0.2 |
| *E. faecalis* ATCC-21212 | 0.78 | 0.78 | 100 |
| MRSA 92-1044 | 25 | 25 | >100 |
| *E. coli* NIHJ JC-2 | 0.2 | 0.0125 | 0.05 |
| *K. pneumoniae* NCTC-9632 | 0.2 | 0.025 | 0.05 |
| *S. marcescens* IFO-12648 | 1.56 | 0.05 | 0.2 |

TABLE 2

$MIC_{80}$ values against clinically isolated meticillin-resistant, highly ciprofloxacin-resistant *Staphylococcus aureus* strains
Inoculum size: $10^6$ cells/ml

| Organism | Test compound | | | VCM | FMOX | CPFX |
|---|---|---|---|---|---|---|
| | (a) | (b) | (c) | | | |
| MRSA (12.5 µg/ml ≧ DMPPC) | 3.13 | 1.56 | 3.13 | 1.56 | 100 | 100 |
| MRSA (100 µg/ml ≧ CPFX) | 3.13 | 1.56 | 3.13 | 1.56 | 100 | >100 |

BEST MODE FOR PRACTICING THE INVENTION

Production examples of the compound of this invention are given below by way of working example.

EXAMPLE 1

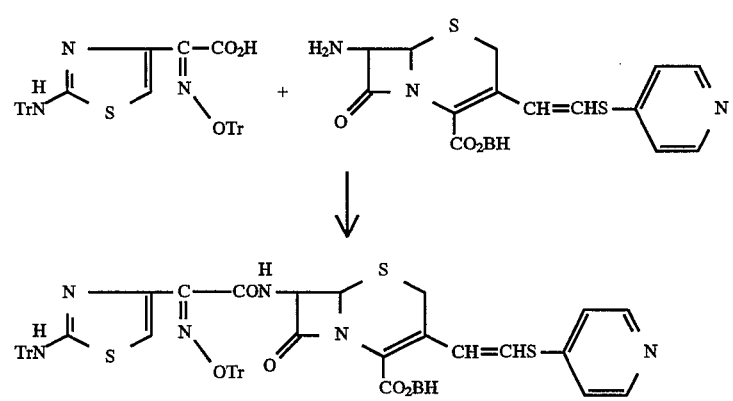

[wherein Tr represents a trityl group and BH represents a benzhydryl group; the same applies hereinafter]

To a solution of benzhydryl 7-amino-3-[2-(4-pyridyl) thiovinyl]-3-cephem-4-carboxylate (a mixture of cis- and trans-isomers) (1.0 g) in a mixture of methylene chloride (10 ml) and dimethylformamide (1.0 ml) were added (Z)-2- trityloxyimino-2-(2-tritylaminothiazol-4-yl)acetic acid (1.46 g) and DCC (dicyclohexylcarbodiimide) (450 mg) and the resultant mixture was stirred at room temperature for 2 hours. After completion of the reaction, the dicyclohexylurea was filtered off and the filtrate was diluted with ethyl acetate (50 ml), washed with saturated aqueous solution of sodium hydrogen carbonate and saturated aqueous solution of sodium chloride and dried over magnesium sulfate. The solvent was then distilled off under reduced pressure to give a crude product (2.65 g). This crude product was chromatographed on a column of silica gel and eluted with benzene-ethyl acetate to provide benzhydryl 7-[2-trityloxyimino-2-(2-tritylaminothiazol-4-yl)acetamido]-3-[2-(4-pyridyl) thiovinyl]-3-cephem-4-carboxylate (1.6 g).

$^1$H-NMR(CDCl$_3$)δ ppm; 3.5–3.7 (2H, m), 5.12 (1H, d, J=5.3 Hz), 6.09 (1H, dd, J=5.3, 8.9 Hz), 6.37 (0.2H, d, J=10.5 Hz), 6.44 (1H, s), 6.59 (0.8H, d, J=15.6 Hz), 6.96 (1H, s), 7.1–7.5 (43H, m), 8.42 (2H, brs), (trans/cis=ca. 4/1)

(763 mg) and the resultant mixture was stirred at room temperature for 65 hours. After completion of the reaction, the solvent was distilled off under reduced pressure and the residue was dried in vacuo. The dried residue was washed with diethyl ether (20 ml) for a total of 3 times to provide benzhydryl 7-[2-trityloxyimino-2-(2-tritylaminothiazol-4-yl)acetamido]-3-[2-(1-carbamoylmethyl-4-pyridinio) thiovinyl]-3-cephem-4-carboxylate iodide (320 mg).

$^1$H-NMR (DMSO-d$_6$)δ ppm; 3.77 (1H, d, J=16.2 Hz), 4.18 (1H, d, J=16.2 Hz), 5.22 (s, 2H), 5.35 (1H, d, J=5.1 Hz), 5.98 (1H, dd, J=5.1, 8.4 Hz), 6.22 (1H, s), 6.92 (1H, s), 7.1–7.7 (42H, m), 7.98 (1H, s), 8.10 (2H, d, J=6.0 Hz), 8.67 (2H, d, J=6.0 Hz), 8.78 (1H, s), 9.95 (1H, d, J=8.4 Hz)

EXAMPLE 2

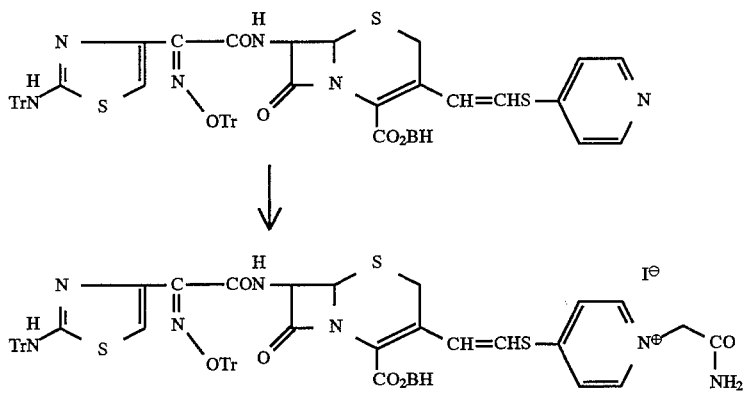

To a solution of benzhydryl 7-[2-trityloxyimino-2-(2-tritylaminothiazol-4-yl)acetamido]-3-[2-(4-pyridyl) thiovinyl]-3-cephem-4-carboxylate (a mixture of cis- and trans-isomers)(238 mg) in a mixture of acetonitrile (11.0 ml) and methylene chloride (5.5 ml) was added iodoacetamide

EXAMPLE 3

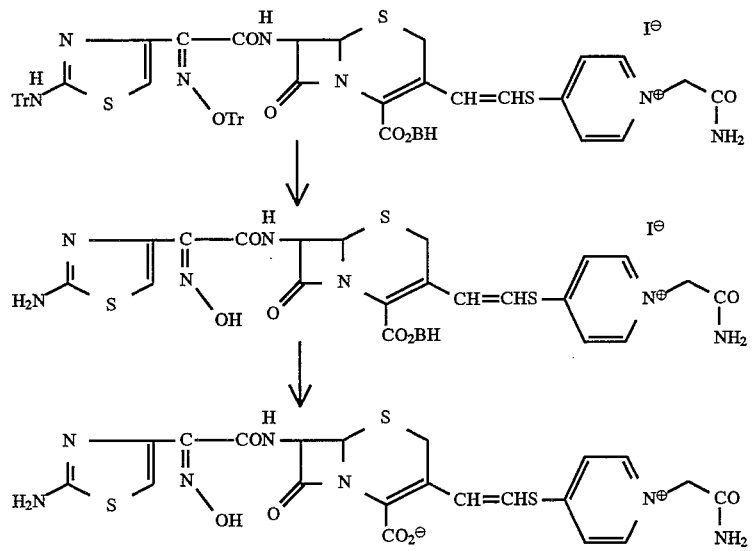

A solution of benzhydryl 7-[2-trityloxyimino-2-(2-trityllaminothiazol-4-yl)acetamido]-3-[2-(1-carbamoyl-methyl-4-pyridinio)thiovinyl]-3-cephem-4-carboxylate iodide (320 mg) in a mixture of acetic acid (7.8 ml) and water (1.05 ml) was warmed at 40°–45° C. for 2 hours. After completion of the reaction, the solvent was distilled off under reduced pressure and diethyl ether (50 ml) was added to provide a precipitate (195 mg). To a solution of this crude detritylated compound [benzhydryl 7-[2-hydroxyimino-2-(2-aminothiazol-4-yl)acetamido]-3-[2-(1-carbamoylmethyl-4-pyridinio)thiovinyl]-3-cephem-4-carboxylate iodide] in methylene chloride (7.0 ml) were added anisole (0.28 ml) and TFA (trifluoroacetic acid) (0.296 ml) at 0° C. and while the temperature was allowed to return to room temperature, the mixture was stirred for 2 hours and 45 minutes. After completion of the reaction, diethyl ether was added, whereby a precipitate (150 mg) was obtained. An aqueous solution of this crude product was adsorbed on Diaion CHP-20P and elution was carried out with water and water-acetonitrile in the order mentioned. The fractions containing the objective compound were pooled, concentrated under reduced pressure and lyophilized to provide 60 mg of 7-[2-hydroxyimino-2-(2-aminothiazol-4-yl)acetamido]-3-[2-(1-carbamoylmethyl-4-pyridinio)thiovinyl]-3-cephem-4-carboxylate (trans-isomer).

$^1$H-NMR (DMSO-d$_6$)δ ppm; 3.53 (1H, d, J=16.2 Hz), 3.74 (1H, d, J=16.2 Hz), 5.07 (1H, d, J=5.1 Hz), 5.20 (2H, brs), 5.63 (1H, dd, J=5.1, 8.4 Hz), 6.48 (1H, d, J=15.3 Hz), 6.64 (1H, s), 7.11 (2H, brs), 7.48 (1H, d, J=15.3 Hz), 7.63 (1H, s), 7.98 (2H, d, J=6.0 Hz), 8.00 (1H, s), 8.60 (2H, d, J=6.0 Hz), 9.43 (1H, d, J=8.4 Hz), 11.7 (1H, s)

trityloxyimino-2-(2-tritylaminothiazol-4-yl)acetamido]-3-[2-(1-methyl-4pyridinio)thiovinyl]-3-cephem-4-carboxylate iodide (4.32 g).

$^1$H-NMR (DMSO-d$_6$)δ ppm; 3.77 (1H, d, J=16.2 Hz), 4.18 (1H, d, J=16.2 Hz), 4.20 (1H, s), 5.35 (1H, d, J=5.1 Hz), 5.98 (1H, dd, J=5.1, 8.4 Hz), 6.62 (1H, s), 6.92 (1H, s), 7.1–7.7 (42H, m), 8.05 (2H, d, J=6.0 Hz), 8.70 (2H, d, J=6.0 Hz), 9.95 (1H, d, J=8.4 Hz)

EXAMPLE 4

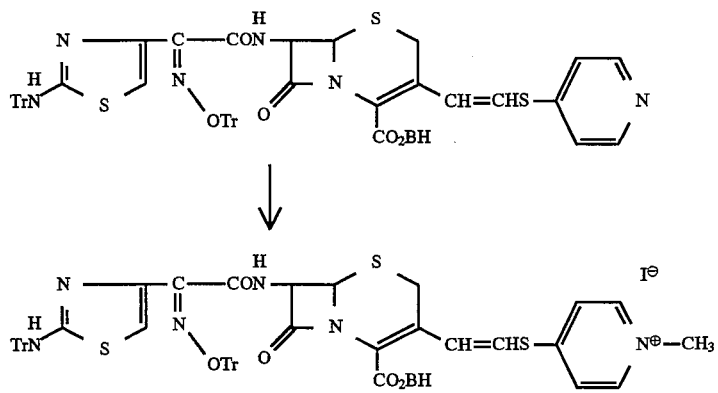

To a solution of benzhydryl 7-[2-trityloxyimino-2-(2-tritylaminothiazol-4-yl)acetamido]-3-[2-(4-pyridyl)thiovinyl]-3-cephem-4-carboxylate (a mixture of cis- and trans-isomers) (4.03 g) in acetonitrile (9.2 ml) and methylene chloride (24 ml) was added methyl iodide (2.21 ml) and the mixture was stirred at room temperature for 22 hours. After completion of the reaction, the reaction mixture was concentrated under reduced pressure and the residue was pulverized with diethyl ether. The resultant powder was recovered by filtration to provide benzhydryl 7-[2-

EXAMPLE 5

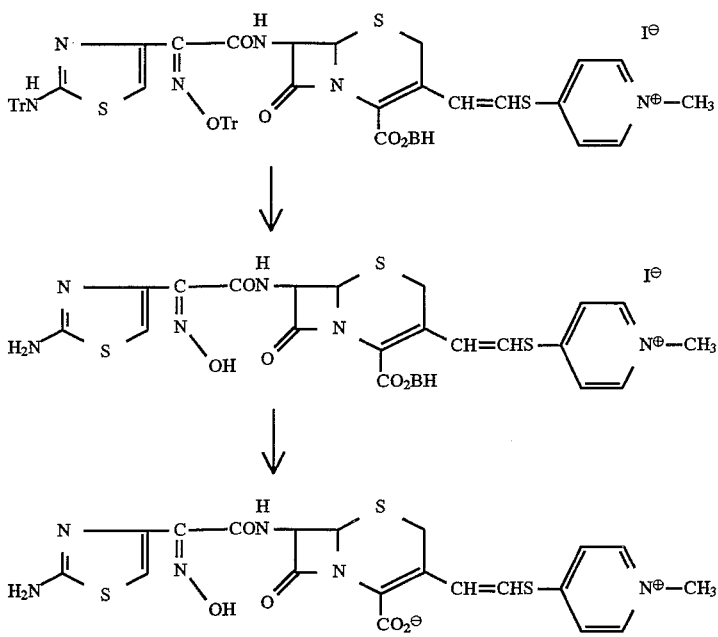

Starting with benzhydryl 7-[2-trityloxyimino-2-(2-tritylaminothiazol-4-yl)acetamido]-3-[2-(1-methyl-4pyridinio)thiovinyl]-3-cephem-4-carboxylate iodide (4.3 g), the procedure of Example 3 was otherwise followed to provide 7-[2-hydroxyimino-2-(2-aminothiazol-4-yl)acetamido]-3-[2-(1-methyl-4-pyridinio)thiovinyl]-3-cephem-4-carboxylate (1.1 g).

$^{1}$H-HMR (DMSO-$d_6$)δ ppm; 3.52 (1H, d, J=16.2 Hz), 3.73 (1H, d, J=16.2 Hz), 4.15 (3H, s), 5.07 (1H, d, J=5.1 Hz), 5.63 (1H, dd, J=5.1, 8.4 Hz), 6.49 (1H, d, J=15.4 Hz), 6.65 (1H, s), 7.1 (2H, brs), 7.48 (1H, d, J=15.4 Hz), 7.95 (2H, d, J=6.0 Hz), 8.61 (2H, d, J=6.0 Hz), 9.44 (1H, d, J=8.4 Hz), 11.32 (1H, s)

EXAMPLE 6

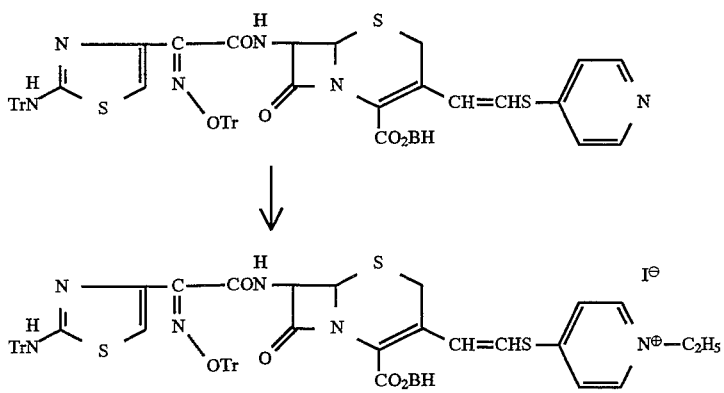

To a solution of benzhydryl 7-[2-trityloxyimino-2-(2-tritylaminothiazol-4-yl)acetamido]-3-[2-pyridyl)thiovinyl]-3-cephem-4-carboxylate (a mixture of cis- and trans- isomers) (1.0 g) in acetonitrile (2.3 ml) and methylene chloride (5.9 ml) were added ethyl bromide (8.5 ml) and sodium iodide (14.9 g) and the mixture was stirred at room temperature for 24 hours. After completion of the reaction, the precipitate was filtered off and the solvent was distilled off under reduced pressure. To the residue was added diethyl ether (100 ml) and the resultant powder was recovered by filtration to provide benzhydryl 7-[2-trityloxyimino-2-(2-tritylaminothiazol-4-yl)acetamido]-3-[2-(1-ethyl-4-pyridinio)thiovinyl]-3-cephem-4-carboxylate iodide (972 mg).

$^{1}$H-NMR (DMSO-$d_6$)δ ppm; 1.47 (3H, t, J=7.2 Hz), 3.76 (1H, d, J=17.7 Hz), 4.16 (1H, d, J=17.7 Hz), 4.48 (2H, q, J=7.2 Hz), 5.35 (1H, d, J=5.1 Hz), 5.98 (1H, dd, J=5.1, 8.1 Hz), 6.62 (1H, s), 6.98 (1H, s), 7.1–7.6 (42H, m), 8.80 (2H, d, J=6.0 Hz), 8.81 (2H, d, J=6.0 Hz), 9.94 (1H, d, J=8.1 Hz),

EXAMPLE 7

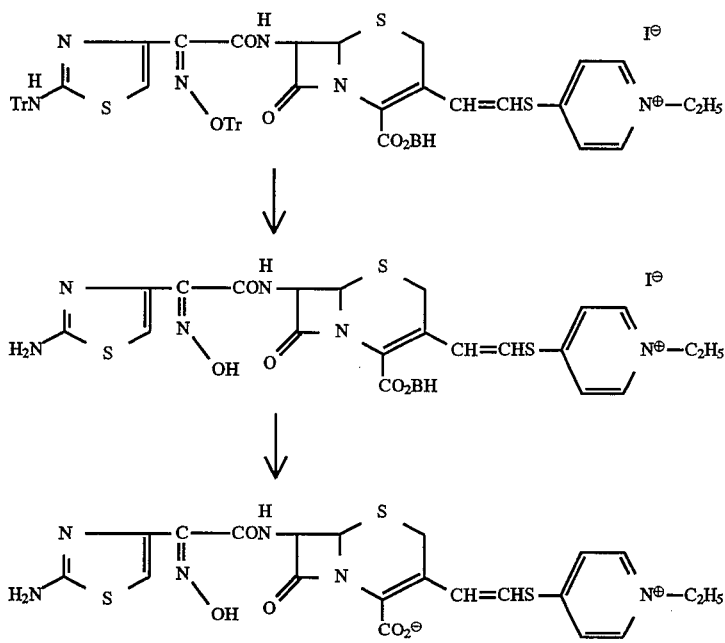

Starting with benzhydryl 7-[2-trityloxyimino-2-(2-tritylaminothiazol-4-yl)acetamido]-3-[2-(1-ethyl-4pyridinio)thiovinyl]-3-cephem-4-carboxylate iodide, the procedure of Example 3 was otherwise followed to provide 7-[2-hydroxyimino-2-(2-aminothiazol-4-yl) acetamido]-3-[2-(1-ethyl-4-pyridinio)thiovinyl]-3-cephem-4-carboxylate.

$^1$H-NMR (DMSO-d$_6$)δ ppm; 1.47 (3H, t, J=7.2 Hz), 3.53 (1H, d, J=1.62 Hz), 3.74 (1H, d, J=16.2 Hz), 5.07 (1H, d, J=5.1 Hz), 5.63 (1H, dd, J=5.1, 8.4 Hz), 4.48 (2H, q, J=7.2 Hz), 6.48 (1H, d, J=15.3 Hz), 6.64 (1H, s), 7.11 (2H, brs), 7.48 (1H, d, J=15.3 Hz), 7.98 (2H, d, J=6.0 Hz), 8.60 (2H, d, J=6.0 Hz), 9.42 (1H, d, J=8.4 Hz), 11.71 (1H, s)

EXAMPLE 8

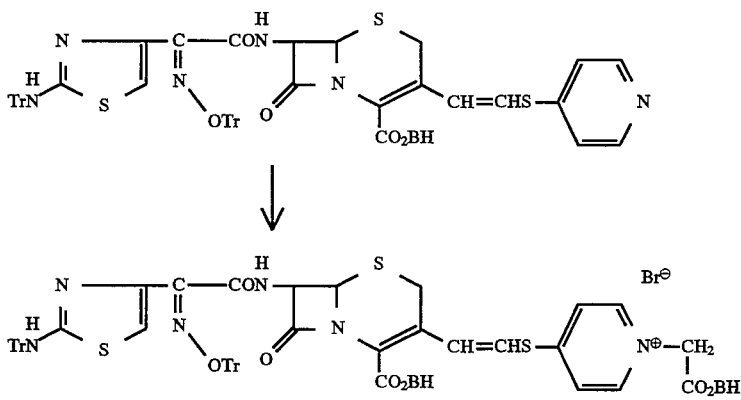

To a solution of benzhydryl 7-[2-trityloxyimino-2-(2-tritylaminothiazol-4-yl)acetamido]-3-[2-(4-pyridyl)thiovinyl]-3-cephem-4-carboxylate (a mixture of cis- and trans-isomers) (1.0 g) in a mixture of acetonitrile (2.3 ml) and methylene chloride (5.9 ml) was added benzhydryl bromoacetate (3.2 g) and the mixture was stirred at room temperature for 12 hours. After completion of the reaction, the solvent was distilled off under reduced pressure and the residue was pulverized with diethyl ether (100 ml). The resultant powder was recovered by filtration to provide benzhydryl 7-[2-trityloxyimino-2-(2-tritylaminothiazol-4-yl)acetoamido]-3-[2-(1-diphenylmethoxycarbonylmethyl-4-pyridinio)thiovinyl]-3-cephem-4-carboxylate bromide (1.2 g).

$^1$H-NMR (DMSO-d$_6$)δ ppm; 3.76 (1H, d, J=17.5 Hz), 4.16 (1H, d, J=17.5 Hz), 5.35 (1H, d, J=5.3 Hz), 5.69 (1H, s), 5.98 (1H, dd, J=5.1, 8.5 Hz), 6.62 (1H, s), 6.93 (1H, s), 6.98 (1H, s), 7.1–7.5 (52H, m), 8.18 (2H, d, J=6.0 Hz), 8.80 (2H, d, J=6.0 Hz), 9.94 (1H, d, J=8.5 Hz)

EXAMPLE 9

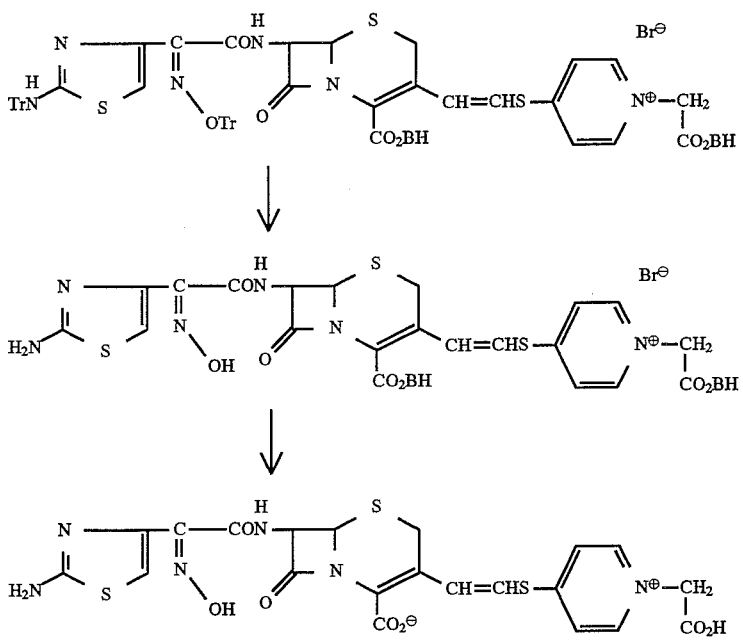

Starting with benzhydryl 7-[2-trityloxyimino-2-(2-tritylaminothiazol-4-yl)acetamido]-3-[2-(1-diphenyl-methoxycarbonylmethyl-4-pyridinio)thiovinyl]-3-cephem-4-carboxylate bromide, the procedure of Example 3 was otherwise followed to provide 7-[2-hydroxyimino-2(2-aminothiazol-4-yl)acetamido]-3-[2-(1-carboxymethyl-4pyridinio)thiovinyl]-3-cephem-4-carboxylate.

$^1$H-NMR (DMSO-d$_6$)δ ppm; 3.52 (1H, d, J=16.0 Hz); 3.73 (1H, d, J=16.0 Hz), 5.07 (1H, d, J=4.8 Hz), 5.64 (1H, dd, J=4.8, 8.4 Hz), 4.69 (2H, s), 6.48 (1H, d, J=15.3 Hz), 6.64 (1H, s), 7.11 (2H, brs), 7.51 (1H, d, J=15.3 Hz), 8.01 (2H, d, J=6.0 Hz), 8.62 (2H, d, J=6.0 Hz), 9.41 (1H, d, J=8.4 Hz), 11.72 (1H, s)

was added to the residue. The resultant powder was recovered by filtration to provide benzhydryl 7-[2-trityloxyimino-2-(2-tritylaminothiazol-4-yl)acetamido]-3-{2-[1-(2-hydroxyethyl)-4-pyridinio]thiovinyl}-3-cephem-4-carboxylate iodide (925 mg).

$^1$H-NMR (DMSO-d$_6$)δ ppm; 3.76 (1H, d, J=17.4 Hz), 4.15 (1H, d, J=17.4 Hz), 3.7–3.8 (2H, m), 4.5–4.6 (2H, m), 5.35 (1H, d, J=5.1 Hz), 5.98 (1H, dd, J=5.1, 8.5 Hz), 6.62 (1H, s), 6.99 (1H, s), 7.1–7.5 (42H, m), 8.18 (2H, d, J=6.0 Hz), 8.80 (2H, d, J=6.0 Hz), 9.94 (1H, d, J=8.5 Hz)

EXAMPLE 10

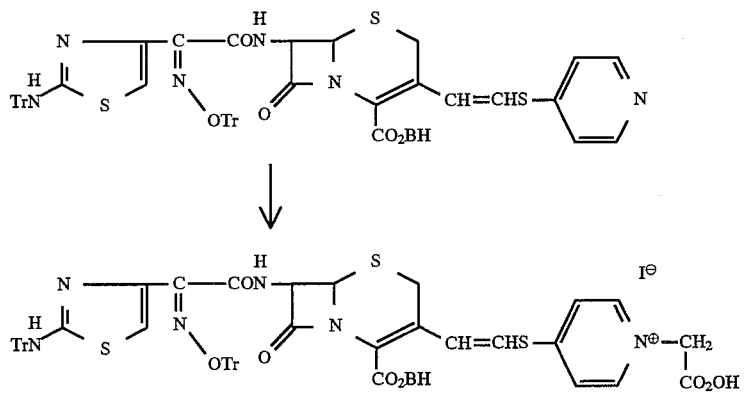

To a solution of benzhydryl 7-[2-trityloxyimino-2-(2-tritylaminothiazol-4-yl)acetamido]-3-[2-(4-pyridyl)thiovinyl]-3-cephem-4-carboxylate (1.2 g) in a mixture of acetonitrile (2.8 ml) and methylene chloride (7.0 ml) was added 2-iodoethanol (8.1 ml) and the mixture was stirred at 40°–50° C. for 50 hours. After completion of the reaction, the solvent was distilled off and diisopropyl ether (100 ml)

EXAMPLE 11

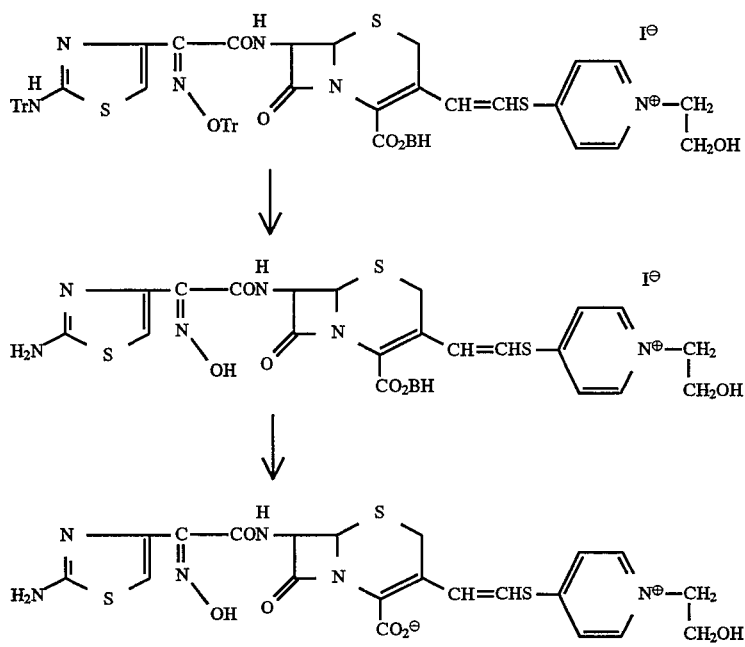

Starting with benzhydryl 7-[2-trityloxyimino-2-(2-tritylaminothiazol-4-yl)acetamido]-3-{2-[1-(2-hydroxyethyl)-4-pyridinio]thiovinyl}-3-cephemcarboxylate iodide, the procedure of Example 3 was otherwise followed to provide 7-[2-hydroxyimino-2-(2-aminothiazol-4yl) acetamido]-3-{2-[1-(2-hydroxyethyl)4-pyridinio] thiovinyl}-3-cephem-4-carboxylate.

$^1$H-NMR (DMSO-d$_6$)δ ppm; 3.52 (1H, d, J=16.2 Hz), 3.74 (1H, d, J=16.2 Hz), 3.8–3.9 (2H, m), 4.6–4.7 (2H, m), 5.07 (1H, d, J=4.8 Hz), 5.65 (1H, dd, J=4.8, 8.5 Hz), 6.48 (1H, d, J=15.4 Hz), 6.65 (1H, s), 7.11 (2H, brs), 7.52 (1H, d, J=15.4 Hz), 7.98 (2H, d, J=6.0 Hz), 8.60 (2H, d, J=6.0 Hz), 9.41 (1H, d, J=8.5 Hz), 11.71 (1H, s)

off under reduced pressure and diethyl ether (100 ml) was added to the residue. The resultant powder was recovered by filtration to provide benzhydryl 7-[2-trityloxyimino-2-(2-tritylaminothiazol-4-yl)acetamido]-3-[2-(1-acetonyl-4-pyridinio)thiovinyl]-3-cephem-4-carboxylate iodide (1.1 g).

$^1$H-NMR (DMSO-d$_6$)δ ppm; 2.28 (3H, s), 3.76 (1H, d, J=17.4 Hz), 4.15 (1H, d, J=17.4 Hz), 5.35 (1H, d, J=4.8 Hz), 5.57 (2H, s), 5.98 (1H, dd, J=4.8, 8.4 Hz), 6.62 (1H, s), 6.99 (1H, s), 7.1–7.5 (42H, m), 8.12 (2H, d, J=6.0 Hz), 8.52 (2H, d, J=6.0 Hz), 9.94 (1H, d, J=8.4 Hz)

EXAMPLE 12

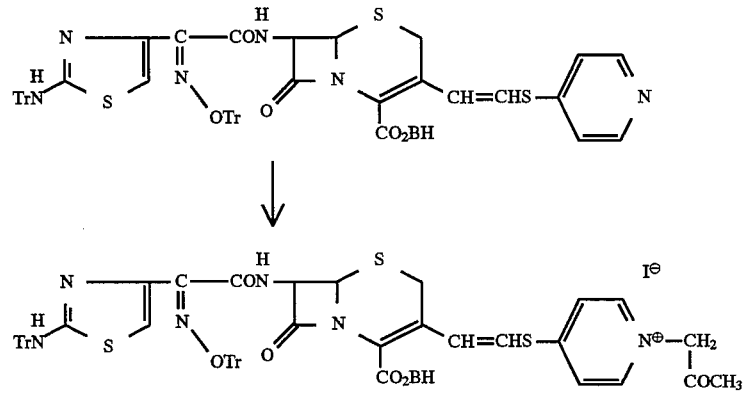

To a solution of benzhydryl 7-[2-trityloxyimino-2-(2-tritylaminothiazol-4-yl)acetamido]-3-[2-(4-pyridyl) thiovinyl]-3-cephem-4-carboxylate (1.0 g) in a mixture of acetonitrile (2.3 ml) and methylene chloride (5.9 ml) were added chloroacetone (0.69 ml) and sodium iodide (1.3 g) and the mixture was reacted at room temperature for 5 hours. After the precipitate was filtered off, the solvent was distilled

EXAMPLE 13

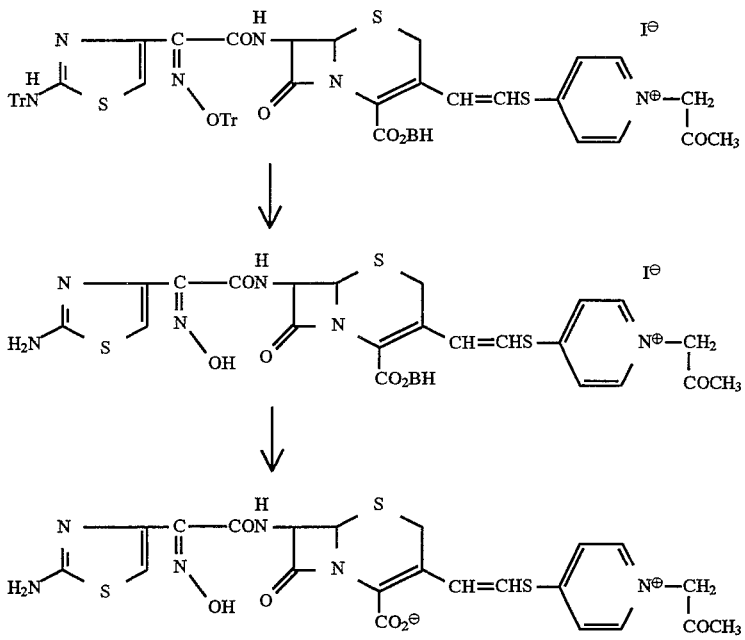

Starting with benzhydryl 7-[2-trityloxyimino-2(2-tritylaminothiazol-4-yl)acetamido]-3-[2-(1-acetonyl-4pyridinio)thiovinyl]-3-cephem-4-carboxylate iodide, the procedure of Example 3 was otherwise repeated to provide 7-[2-hydroxyimino-2-(2-aminothiazol-4-yl)acetamido]-3-[2-(1-acetonyl-4-pyridinio)thiovinyl]-3-cephem-4-carboxylate.

$^1$H-NMR (DMSO-d$_6$)δ ppm; 2.28 (3H, s), 3.54 (1H, d, J=16.0 Hz), 3.75 (1H, d, J=16.0 Hz), 5.08 (1H, d, J=4.8 Hz), 5.64 (1H, dd, J=4.8, 8.4 Hz), 5.57 (2H, s), 6.48 (1H, d, J=15.3 Hz), 6.64 (1H, s), 7.12 (2H, brs), 7.50 (1H, d, J=15.3 Hz), 8.02 (2H, d, J=6.0 Hz), 8.50 (2H, d, J=6.0 Hz), 9.42 (1H, d, J=8.4 Hz), 11.70 (1H, s)

EXAMPLE 14

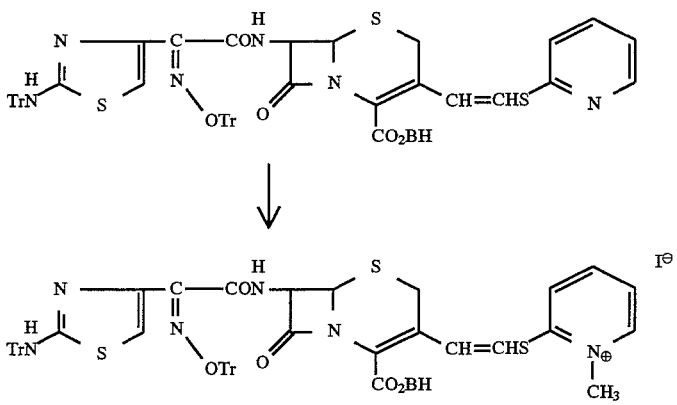

To a solution of benzhydryl 7-[2-trityloxyimino-2-(2-tritylaminothiazol-4-yl)acetamido]-3-[2-(2-pyridyl) thiovinyl]-3-cephem-4-carboxylate (2.4 g) in a mixture of acetonitrile (12 ml) and methylene chloride (4.8 ml) was added methyl iodide (18.7 ml) and the mixture was stirred at room temperature for 3 days. After completion of the reaction, the reaction mixture was concentrated under reduced pressure and the residue was dissolved in chloroform (38 ml) and dripped into diisopropyl ether (120 ml). The resultant precipitate was recovered to provide benzhydryl 7-[2-trityloxyimino-2-(2-tritylaminothiazol-4-yl) acetamido]-3-[2-(1-methyl-2-pyridinio)thiovinyl]-3-cephem-4-carboxylate iodide (3.5 g).

$^1$H-NMR (DMSO-d$_6$)δ ppm; 3.77 (1H, d, J=16.8 Hz), 4.15 (1H, d, J=16.8 Hz), 4.20 (3H, s), 5.25 (1H, d, J=4.8 Hz), 5.80 (1H, dd, J=4.8, 8.1 Hz), 6.68 (1H, s), 6.97 (1H, s), 7.1–7.7 (46H, m), 8.94 (1H, s), 9.63 (1H, d, J=8.1 Hz)

EXAMPLE 15

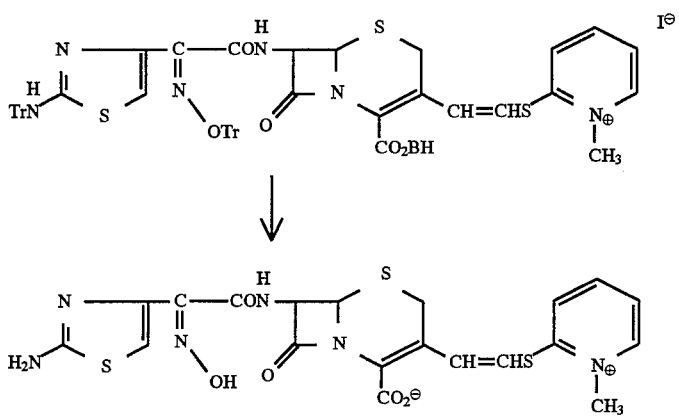

To a solution of benzhydryl 7-[2-trityloxyimino-2-(2-tritylaminothiazol-4-yl)acetamido]-3-[2-(1-methyl-2-pyridinio)thiovinyl]-3-cephem-4-carboxylate iodide (2.5 g) in chloroform (7.1 ml) were added 88% formic acid (4.7 ml) and concentrated hydrochloric acid (0.46 ml) and the mixture was stirred at 25° C. for 3.5 hours. After completion of the reaction, chloroform (14.5 ml) was added. After phase separation, the upper layer was washed with chloroform (14.5 ml×3 times) and the formic acid layer was dripped into a mixture of diisopropyl ether (13.4 ml) and acetone (49 ml). The resultant precipitate was washed with acetone to give the deprotected hydrochloride (1.7 g). This product was then dissolved in 0.1 N-hydrochloric acid (60 ml) and, in the routine manner, purified by Diaion HP-21 column chromatography (eluent: acetonitrile-water) and lyophilized to provide 7-[2-hydroxyimino-2-(2-aminothiazol-4-yl)acetamido]-3-[2-(1-methyl-2-pyridinio)thiovinyl]-3-cephem-4-carboxylate (600 mg).

$^1$H-NMR (DMSO-d$_6$)δ ppm; 3.54 (1H, d, J=16.8 Hz), 3.66 (1H, d, J=16.8 Hz), 4.10 (3H, s), 5.05 (1H, d, J=4.8 Hz), 5.57 (1H, dd, J=4.8, 8.1Hz), 6.72 (1H, d, J=15.8 Hz), 6.73 (1H, s), 7.14 (1H, dd, J=0.9, 4.8 Hz), 7.19 (2H, s), 7.31 (1H, d, J=15.8 Hz), 7.68 (1H, dd, J=1.8, 8.1 Hz), 8.42 (1H, dd, J=2.7, 4.8 Hz), 7.35 (1H, d, J=8.4 Hz), 9.55 (1H, d, J=8.1 Hz), 11.6 (1H, brs)

thiovinyl]-3-cephem-4-carboxylate (1.0 g) in a mixture of acetonitrile (5.9 ml) and methylene chloride (2.3 ml) were added 4-(chloroacetyl)catechol (895 mg) and sodium iodide (750 mg) and the mixture was stirred at room temperature for 6.5 hours. After completion of the reaction, methylene chloride (30 ml) was added and the insoluble matter was filtered off. The filtrate was concentrated under reduced pressure and the solvent was distilled off. The residue was dissolved in chloroform (50 ml), the solution was dripped into diisopropyl ether (50 ml) and the resultant precipitate was recovered to provide benzhydryl 7-[2-trityloxyimino-2-(2-tritylaminothiazol-4-yl)acetamido]-3-{2-[1-(3,4-dihydroxyphenylcarbonylmethyl)-4-pyridinio]thiovinyl}-3-cephem-4-carboxylate iodide (1.05 g).

$^1$H-NMR (DMSO-d$_6$)δ ppm; 3.77 (1H, d, J=17 Hz), 4.18 (1H, d, J=17 Hz), 5.35 (1H, d, J=5.1 Hz), 5.98 (1H, dd, J=5.1, 8.1 Hz), 6.16 (2H, s), 6.61 (1H, s), 6.99 (1H, s), 6.9–7.5 (45H, m), 8.15 (2H, d, J=6.9 Hz), 8.74 (2H, d, J=6.9 Hz), 8.78 (1H, s), 9.94 (1H, d, J=8.1 Hz),

EXAMPLE 16

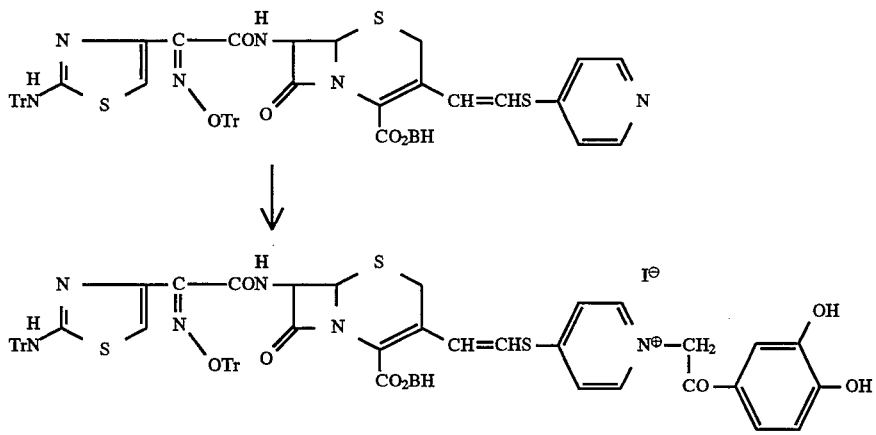

To a solution of benzhydryl 7-[2-trityloxyimino-2-(2-tritylaminothiazol-4-yl)acetamido]-3-[2-(4-pyridyl)

EXAMPLE 17

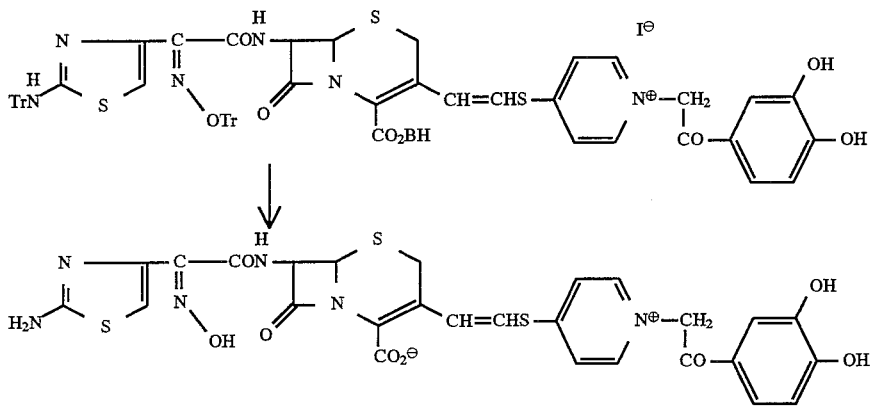

To a solution of benzhydryl 7-[2-trityloxyimino-2-(2-tritylaminothiazol-4-yl)acetamido]-3-{2-[1-(3,4-dihydroxyphenylcarbonylmethyl)-4-pyridinio]thiovinyl}-3-cephem-4-carboxylate iodide (1.0 g) in chloroform (3.0 ml) were added 88% formic acid (2 ml) and concentrated hydrochloric acid (0.18 ml) and the mixture was stirred at 25° C. for 2.5 hours. After completion of the reaction, chloroform (15 ml) was added. After phase separation, the upper layer was washed with chloroform (15 ml×3) and the formic acid layer was then dripped into a mixture of diisopropyl ether (5.4 ml) and acetone (20 ml). The resultant precipitate was washed with acetone to give the crude compound (458 mg) as a hydrochloride. This product was then dissolved in 0.1 N-hydrochloric acid (100 ml) and, in the routine manner, purified by Diaion HP-21 column chromatography (eluent: acetonitrile-water) and lyophilized to provide 7-[2-hydroxyimino-2-(2-aminothiazol-4-yl)acetamido]-3-{2-[1-(3,4-dihydroxyphenylcarbonylmethyl)-4-pyridinio]-thiovinyl}3-cephem-4-carboxylate (57 mg).

$^1$H-NMR (DMSO-$d_6$)δ ppm; 3.79 (1H, d, J=17.1 Hz), 3.56 (1H, d, J=17.1 Hz), 5.07 (1H, d, J=5.1 Hz), 5.65 (1H, dd, J=5.1, 8.1 Hz), 6.13 (2H, brs), 6.57 (1H, d, J=15.3 Hz), 6.65 (1H, s), 6.92 (1H, d, J=8.1 Hz), 7.11 (2H, brs), 7.43 (2H, m), 7.51 (1H, d, J=15.3 Hz), 8.05 (2H, d, J=6.9 Hz), 8.59 (2H, d, J=6.9 Hz), 9.44 (1H, d, J=8.1 Hz)

acetonitrile (9.6 ml) and methylene chloride (3.7 ml) were added benzhydryl 5-bromovalerate (11.0 g) and sodium iodide (4.84 g) and the mixture was stirred at 45° C. for 47.5 hours. After completion of the reaction, methylene chloride (48 ml) was added and the insoluble matter was filtered off. The filtrate was concentrated under reduced pressure and the solvent was then distilled off. The residue was dissolved in chloroform (7 ml), the solution was dripped in diisopropyl ether (75 ml) and the resultant precipitate was separated to provide benzhydryl 7-[2-trityloxyimino-2-(2-tritylaminothiazol-4-yl)acetamido]-3-{2-[1-(4-diphenylmethoxycarbonylbutyl)-4-pyridinio]thiovinyl}-3-cephem-4-carboxylate iodide (2.02 g), $^1$H-NMR (DMSO-$d_6$)δ ppm; 1.42–1.59 (2H, m), 1.79–1.92 (2H, m), 2.50 (2H, t, J=7.2 Hz), 3.75 (1H, d, J=17.4 Hz), 4.14 (1H, d, J=17.4 Hz), 4.45 (2H, t, J=7.2 Hz), 5.34 (1H, d, J=4.8 Hz), 5.98 (1H, dd, J=4.8, 8.1 Hz), 6.62 (1H, s), 6.78 (1H, s), 6.97 (1H, s), 7.0–7.6 (52H, m), 8.08 (2H, d, J=6.9 Hz), 8.78 (2H, d, J=6.9 Hz), 9.92 (1H, d, J=8.1 Hz)

EXAMPLE 18

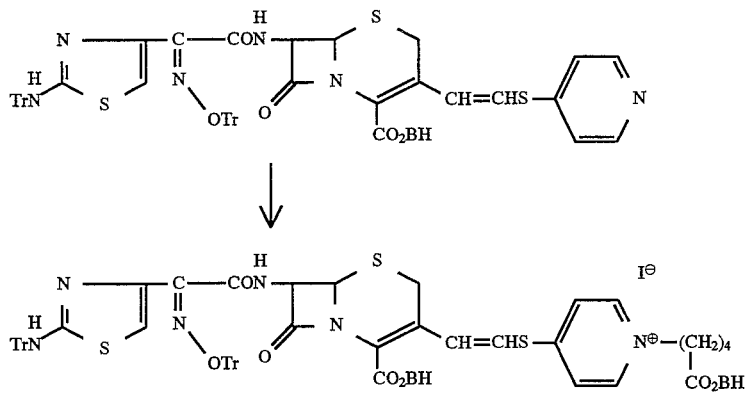

To a solution of benzhydryl 7-[2-trityloxyimino-2-(2-tritylaminothiazol-4-yl)acetamido]-3-[2-(4-pyridyl)thiovinyl]-3-cephem-4-carboxylate (1.6 g) in a mixture of

EXAMPLE 19

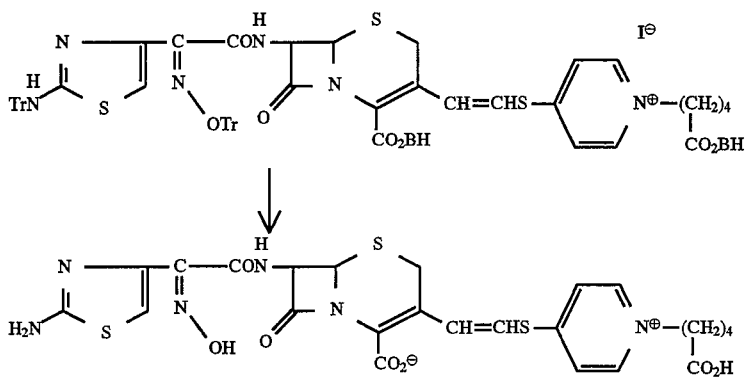

To a solution of benzhydryl 7-[2-trityloxyimino-2-(2-tritylaminothiazol-4-yl)acetamido]-3-{2-[1-(4-diphenylmethoxycarbonylbutyl)-4-pyridinio]thiovinyl}-3-cephem-4-carboxylate iodide (1.8 g) in chloroform (4.8 ml) were added 88% formic acid (2 ml) and concentrated hydrochloric acid (0.3 ml) and the mixture was stirred at 25° C. for 3 hours. After completion of the reaction, chloroform (24 ml) was added and after phase separation, the upper layer was washed with chloroform (24 ml×3). The formic acid layer was dripped into a mixture of diisopropyl ether (8.4 ml) and acetone (31 ml) and the resultant precipitate was washed with acetone to give hydrochloride (465 mg). This product was dissolved in 0.1N-hydrochloric acid (100 ml) and, in the routine manner, purified by Diaion HP-21 column chromatography (eluent: acetonitrile-water) and lyophilized to provide 7-[2-hydroxyimino-2-(2-aminothiazol-4-yl)acetamido]-3-{2-[1-(4-carboxybutyl)-4-pyridinio]thiovinyl}-3-cephem-4carboxylate (167 mg).

$^1$H-NMR (DMSO-$d_6$)δ ppm; 1.44 (2H, m), 1.84 (2H, m), 2.25 (2H, t, J=7.2 Hz), 4.34 (2H, t, J=7.2 Hz), 5.08 (1H, d, J=4.8 Hz), 5.65 (1H, dd, J=4.8, 8.1 Hz), 6.50 (1H, d, J=15.3 Hz), 6.64 (1H, s), 7.12 (2H, brs), 7.46 (1H, d, J=15.3 Hz), 7.98 (2H, d, J=6.9 Hz), 8.74 (2H, d, J=6.9 Hz), 9.44 (1H, d, J=8.1 Hz)

of Example 18 was otherwise followed to provide benzhydryl 7-[2-trityloxyimino-2-(2-tritylaminothiazol-4-yl)acetamido]-3-{2-[1-(4-diphenylmethoxycarbonylbenzyl)-4-pyridinio]thiovinyl}-3-cephem-4-carboxylate iodide.

$^1$H-NMR (DMSO-$d_6$)δ ppm; 3.71 (1H, d, J=17.0 Hz), 4.12 (1H, d, J=17.0 Hz), 5.31 (1H, d, J=5.4 Hz), 5.82 (2H, brs), 5.98 (1H, dd, J=5.4, 8.1 Hz), 6.61 (1H, s), 6.98 (1H, s), 7.03 (1H, s), 7.1–7.5 (52H, m), 7.61 (2H, d, J=8.7 Hz), 8.11 (2H, d, J=8.1 Hz), 8.13 (2H, d, J=6.9 Hz), 8.78 (1H, s), 8.91 (2H, d, J=6.9 Hz), 9.92 (1H, d, J=8.1 Hz)

EXAMPLE 20

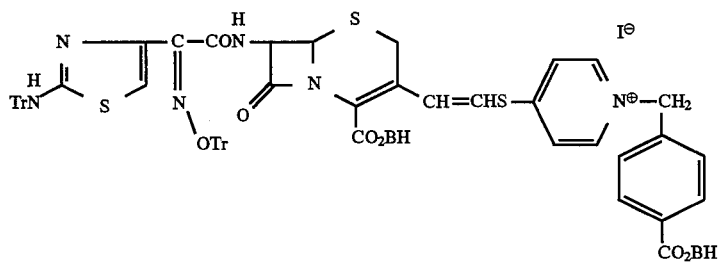

Using benzhydryl 7-[2-trityloxyimino-2-(2-tritylaminothiazol-4-yl)acetamide]-3-[2-(4-pyridyl)thiovinyl]-3-cephem-4-carboxylate, benzhydryl p-chloromethylbenzoate and sodium iodide, the procedure

EXAMPLE 21

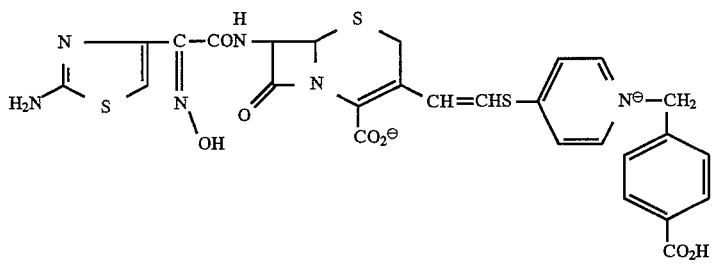

Using benzhydryl 7-[2-trityloxyimino-2-(2-tritylaminothiazol-4-yl)acetamido]-3-{2-[1-(4-diphenyl-methoxycarbonylbenzyl)-4-pyridinio]thiovinyl}-3-cephem-4-carboxylate iodide, the procedure of Example 19 was otherwise followed to provide 7-[2-hydroxyimino-2-(2-aminothiazol-4-yl)acetamido]-3-{2-[1-(4-carboxybenzyl)-4-pyridinio]thiovinyl}-3-cephem-4-carboxylate.

$^1$H-NMR (DMSO-d$_6$)δ ppm; 3.52 (1H, d, J=17.0 Hz), 3.75 (1H, d, J=17.0 Hz), 5.07 (1H, d, J=5.4 Hz), 5.65 (1H, dd, J=5.4, 8.1 Hz), 5.76 (2H, brs), 6.51 (1H, d, J=15.3 Hz), 6.64 (1H, s), 7.12 (2H, brs), 7.51 (2H, d, J=8.7 Hz), 7.94 (2H, d, J=8.1 Hz), 8.01 (2H, d, J=6.9 Hz), 8.84 (2H, d, J=6.9 Hz), 9.44 (1H, d, J=8.1 Hz)

5.67 (1H, dd, J=5.1, 8.1 Hz), 6.62 (1H, s), 6.75 (1H, s), 6.98 (1H, s), 7.0–7.5 (56H, m), 8.09 (2H, d, J=6.9 Hz), 8.79 (1H, s), 8.9 (2H, d, J=6.9 Hz), 9.94 (1H, d, J=8.1 Hz)

EXAMPLE 22

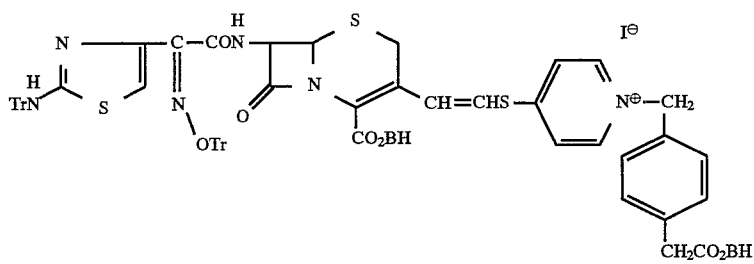

Using benzhydryl 7-[2-trityloxyimino-2-(2-tritylaminothiazol-4-yl)acetamido]-3-[2-(4-pyridyl) thiovinyl]-3-cephem-4-carboxylate, benzhydryl p-chloromethylphenylacetate and sodium iodide, the procedure of Example 18 was otherwise followed to provide benzhydryl 7-[2-trityloxyimino-2-(2-tritylaminothiazol-4-yl)acetamido]-3-{2-[1-(4-diphenylmethoxycarbonylmethylbenzyl)-4-pyridinio]thiovinyl}-3-cephem-4-carboxylate iodide.

$^1$H-NMR (DMSO-d$_6$)δ ppm; 3.72 (1H, d, J=16.8 Hz), 3.83 (2H, s), 4.13 (1H, d, J=16.8 Hz), 5.33 (1H, d, J=5.1 Hz),

EXAMPLE 23

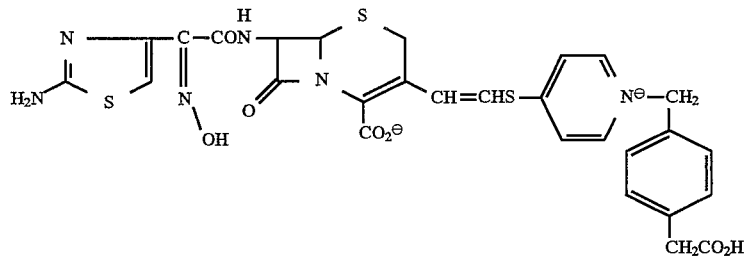

Starting with benzhydryl 7-[2-trityloxyimino-2-(2-tritylaminothiazol-4-yl)acetamido]-3-{2-[1-(4-diphenylmethoxycarbonylmethylbenzyl)-4-pyridinio] thiovinyl}-3-cephem-4-carboxylate iodide, the procedure of Example 19 was otherwise followed to provide 7-[2-hydroxyimino-2-(2-aminothiazol-4-yl)acetamido]-3-{2-[1-(4-carboxymethylbenzyl)-4-pyridinio]thiovinyl}-3-cephem-4-carboxylate.

¹H-NMR (DMSO-d₆+D₂O)δ ppm; 3.22 (2H, s), 3.50 (1H, d, J=16.8 Hz), 3.73 (1H, d, J=16.8 Hz), 5.05 (1H, d, J=5.1Hz), 5.56 (2H, brs), 5.64 (1H, d, J=5.1 Hz), 6.49 (1H, d, J=15.3 Hz), 6.64 (1H, s), 7.2–7.3 (4H, m), 7.45 (1H, d, J=15.3 Hz), 7.86 (2H, d, J=6.9 Hz), 8.74 (2H, d, J=6.9 Hz)

¹H-NMR (DMSO-d₆)δ ppm; 1.03 (3H, t, J=7.0 Hz), 1.22 (3H, t, J=7.0 Hz), 3.31 (4H, m), 3.75 (1H, d, J=16.8 Hz), 4.14 (1H, d, J=16.8 Hz), 5.33 (1H, d, J=4.8 Hz), 5.57 (2H, brs), 5.98 (1H, dd, J=4.8, 8.0 Hz), 6.61 (1H, s), 6.98 (1H, s), 7.05–7.50 (42 H, m), 8.10 (2H, d, J=6.0 Hz), 8.64 (2H, d, J=6.0 Hz), 6.79 (1H, s), 9.93 (1H, d, J=8.0 Hz)

EXAMPLE 24

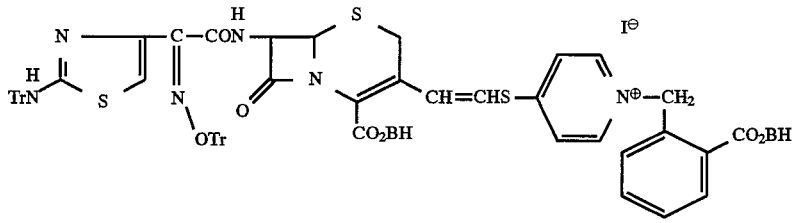

Using benzhydryl 7-[2-trityloxyimino-2-(2-tritylaminothiazol-4-yl)acetamido]-3-[2-(4-pyridyl)thiovinyl]-3-cephem-4-carboxylate and benzhydryl o-iodomethylbenzoate, the procedure of Example 18 was otherwise followed to provide benzhydryl 7-[2-trityloxyimino-2-(2-tritylaminothiazol-4-yl)acetamido]-3-{2-[1-(2-diphenylmethoxycarbonylbenzyl)-4-pyridinio]thiovinyl}-3-cephem-4-carboxylate iodide.

¹H-NMR (DMSO-d₆)δ ppm; 3.75 (1H, d, J=17.1 Hz), 4.14 (1H, d, J=17.1Hz), 5.34 (1H, d, J=5.1 Hz), 5.93–6.0 (1H, m), 6.01 (2H, brs), 6.61 (1H, s), 6.97 (1H, s), 6.98 (1H, s), 7.0–8.5 (46H, m), 8.03 (2H, d, J=6.9 Hz), 8.68 (1H, d, J=6.9 Hz), 8.78 (1H, s), 9.93 (1H, d, J=8.1 Hz)

EXAMPLE 25

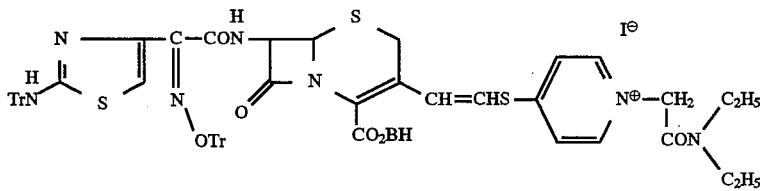

Using benzhydryl 7-[2-trityloxyimino-2-(2-tritylaminothiazol-4-yl)acetamido]-3-[2-(4-pyridyl)thiovinyl]-3-cephem-4-carboxylate, N-N-diethyl-2-chloroacetamide and sodium iodide, the procedure of Example 18 was otherwise followed to provide benzhydryl 7-[2-trityloxyimino-2-(2-tritylaminothiazol-4-yl)acetamido]-3-{2-[1-(N,N-diethylaminocarbonylmethyl)-4-pyridinio]thiovinyl}-3-cephem-4-carboxylate iodide.

EXAMPLE 26

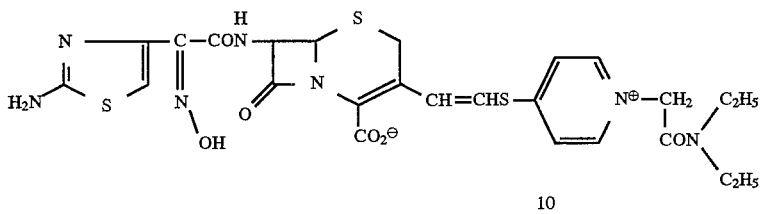

Starting with benzhydryl 7-[2-trityloxyimino-2-(2-tritylaminothiazol-4-yl)acetamido]-3-{2-[1-(N,N-diethylaminocarbonylmethyl)-4-pyridinio]thiovinyl}-3-cephem-4-carboxylate iodide, the procedure of Example 19 was otherwise repeated to provide 7-[2-hydroxyimino-2-(2-aminothiazol-4-yl)acetamido]-3-{2-[1-(N,N-diethylaminocarbonylmethyl)-4-pyridinio]thiovinyl}-3-cephem-4-carboxylate.

$^1$H-NMR (DMSO-$d_6$)δ ppm; 1.03 (3H, t, J=7.0 Hz), 1.21 (3H, t, J=7.0 Hz), 3.33 (4H, m), 3.54 (1H, d, J=16.8 Hz), 3.74 (1H, d, J=16.8 Hz), 5.08 (1H, d, J=4.8 Hz), 5.56 (2H, brs), 5.65 (1H, dd, J=4.8, 8.0 Hz), 6.52 (1H, d, J=15.3 Hz), 6.64 (1H, s), 7.12 (2H, brs), 7.47 (1H, d, J=15.3 Hz), 8.00 (2H, d, J=6.0 Hz), 8.59 (2H, d, J=6.0 Hz), 9.44 (1H, d, J=8.0 Hz), 11.38 (1H, brs)

EXAMPLE 27

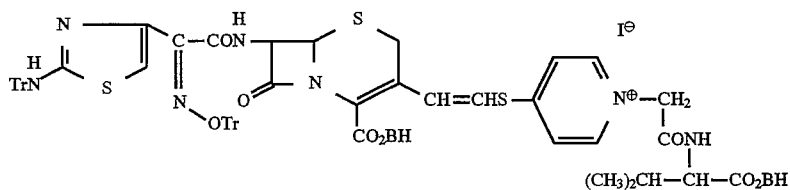

Using benzhydryl 7-[2-trityloxyimino-2-(2-tritylaminothiazol-4-yl)acetamido]-3-[2-(4-pyridyl)thiovinyl]-3-cephem-4-carboxylate, chloroacetyl-valine benzhydryl ester and sodium iodide, the procedure of Example 18 was otherwise followed to provide benzhydryl 7-[2-trityloxyimino-2-(2-tritylaminothiazol-4-yl)acetamido]-3-{2-[1-(1-diphenylmethoxycarbonyl-2-methylpropyl-aminocarbonylmethyl)-4-pyridinio]thiovinyl}-3-cephem-4-carboxylate iodide.

$^1$H-NMR (DMSO-$d_6$)δ ppm; 0.83 (3H, d, J=3.0 Hz), 0.85 (3H, d, J=3.0 Hz), 2.20 (1H, m), 3.74 (1H, d, J=16.8 Hz), 4.15 (1H, d,J=16.8 Hz), 4.40 (1H, dd, J=5.2, 8.4 Hz), 5.34 (1H, d, J=5.4 Hz), 5.38 (2H, brs), 5.97 (1H, dd, J=5.4, 8.4 Hz), 6.61 (1H, s), 6.81 (1H, s), 6.99 (1H, s), 7.0–7.5 (52H, m), 8.08 (2H, d, J=7.2 Hz), 8.64 (2H, d, J=7.2 Hz), 8.78 (1H, s), 8.95 (1H, d, J=8.4 Hz)

Using benzhydryl 7-[2-trityloxyimino-2-(2-tritylaminothiazol-4-yl)acetamido]-3-{2-[1-(1-diphenylmethoxycarbonyl-2-methylpropylaminocarbonylmethyl)-4-pyridinio]thiovinyl}-3-cephem-4-carboxylate iodide, the procedure of Example 19 was otherwise followed to provide 7-[2-hydroxyimino-2-(2-aminothiazol-4-yl)acetamido]-3-{2-[1-(1-carboxyl-2-methylpropylaminocarbonylmethyl)-4-pyridinio ]thiovinyl }-3-cephem-4-carboxylate.

$^1$H-NMR (DMSO-$d_6$)δ ppm; 0.87 (3H, d, J=3.0 Hz), 0.89 (3H, d, J=3.0 Hz), 2.08 (1H, m), 3.55 (1H, d, J=16.8 Hz), 3.78 (1H, d, J=16.8 Hz), 4.15 (1H, dd, J=5.2, 8.4 Hz), 5.09 (1H, d, J=5.4 Hz), 5.34 (2H, brs), 5.67 (1H, dd, J=4.5, 8.4 Hz), 6.58 (1H, d, J=15.6 Hz), 6.64 (1H, s), 7.14 (2H, brs), 7.46 (1H, d, J=15.6 Hz), 7.99 (2H, d, J=7.2 Hz), 8.62 (2H, d, J=7.2 Hz), 8.88 (1H, d, J=8.4 Hz), 9.45 (1H, d, J=8.4 Hz)

EXAMPLE 28

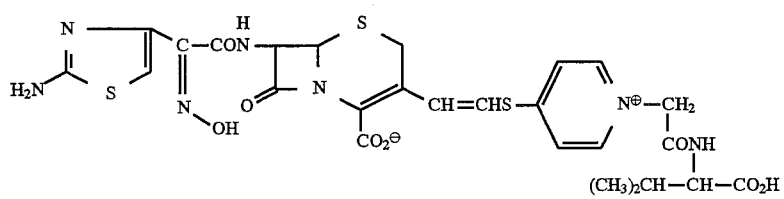

EXAMPLE 29

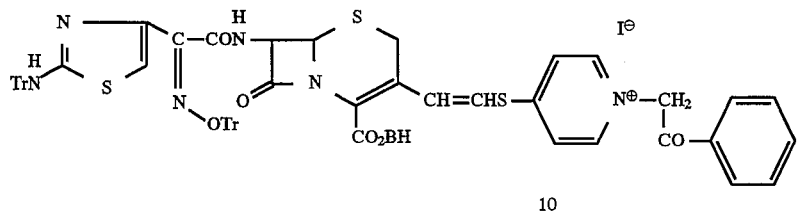

Using benzhydryl 7-[2-trityloxyimino-2-(2-tritylaminothiazol-4-yl)acetamido]-3-[2-(4-pyridyl)thiovinyl]-3-cephem-4-carboxylate, phenacyl chloride and sodium iodide, the procedure of Example 18 was otherwise followed to provide benzhydryl 7-[2-trityloxyimino-2-(2-tritylaminothiazol-4-yl)acetamido]-3-[2-(1-phenylcarbonylmethyl-4-pyridinio)thiovinyl]-3-cephem-4-carboxylate iodide.

$^1$H-NMR (DMSO-$d_6$)δ ppm; 3.78 (1H, d, J=16.9 Hz), 4.17 (1H, d, J=16.9 Hz), 5.35 (1H, d, J=5.0 Hz), 5.98 (1H, dd, J=5.0, 8.1 Hz), 6.30 (2H, brs), 6.62 (1H, s), 6.99 (1H, s), 7.0–8.1 (47H, m), 8.19 (2H, d, J=6.9 Hz), 8.68 (2H, d, J=6.9 Hz), 8.78 (1H, s), 9.95 (1H, d, J=8.1 Hz)

thiovinyl]-3-cephem-4-carboxylate bromide, the procedure of Example 19 was otherwise followed to provide 7-[2-hydroxyimino-2-(2-aminothiazol-4-yl)acetamido]-3-[2-(1-allyl-4-pyridinio)thiovinyl-3-cephem-4-carboxylate.

$^1$H-NMR (DMSO-$d_6$)δ ppm; 3.54 (1H, d, J=16.8 Hz), 3.73 (1H, d, J=16.8 Hz), 5.06 (1H, d, J=4.8 Hz), 5.08 (2H, d, J=6.0 Hz), 5.31 (1H, d, J=17.1 Hz), 5.38 (1H, d, J=10.8 Hz), 5.64 (1H, dd, J=4.8, 8.1 Hz), 6.06 (1H, m), 6.47 (1H, d, J=15.3 Hz), 6.64 (1H, s), 7.10 (2H, brs), 7.48 (1H, d, J=15.3 Hz), 7.99 (2H, d, J=7.2 Hz), 8.66 (2H, d, J=7.2 Hz), 9.45 (1H, d, J=8.1 Hz)

EXAMPLE 30

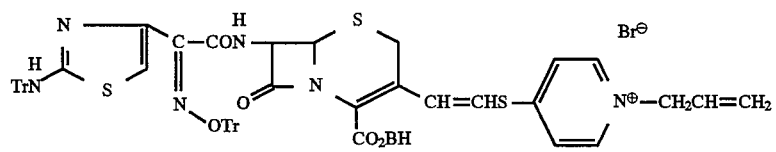

Using benzhydryl 7-[2-trityloxyimino-2-(2-tritylaminothiazol-4-yl)acetamido]-3-[2-(4-(4-pyridyl)thiovinyl]-3-cephem-4-carboxylate and allyl bromide, the procedure of Example 18 was otherwise followed to provide benzhydryl 7-[2-trityloxyimino-2-(2-tritylaminothiazol-4-yl)acetamido]-3-[2-(1-allyl-4-pyridinio)thiovinyl]-3-cephem-4-carboxylate bromide.

$^1$H-NMR (DMSO-$d_6$)δ ppm; 3.75 (1H, d, J=16.8 Hz), 4.16 (1H, d, J=16.8 Hz), 5.11 (2H, d, J=6.0 Hz), 5.34 (1H, d, J=4.8 Hz), 5.3–5.4 (2H, m), 5.96 (1H, dd, J=4.8, 8.1 Hz), 6.01–6.19 (1H, m), 6.62 (1H, s), 6.98 (1H, s), 7.0–7.5 (42H, m), 8.10 (2H, d, J=7.2 Hz), 8.72 (2H, d, J=7.2 Hz), 8.78 (1H, s), 9.95 (1H, d, J=8.1 Hz)

EXAMPLE 31

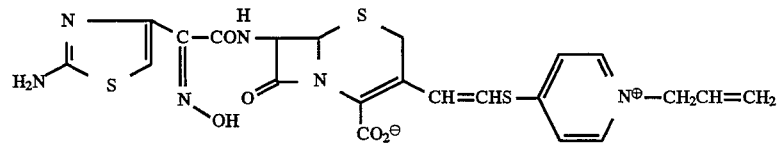

Using benzhydryl 7-[2-trityloxyimino-2-(2-tritylaminothiazol-4-yl)acetamido]-3-[2-(1-allyl-4pyridinio)

EXAMPLE 32

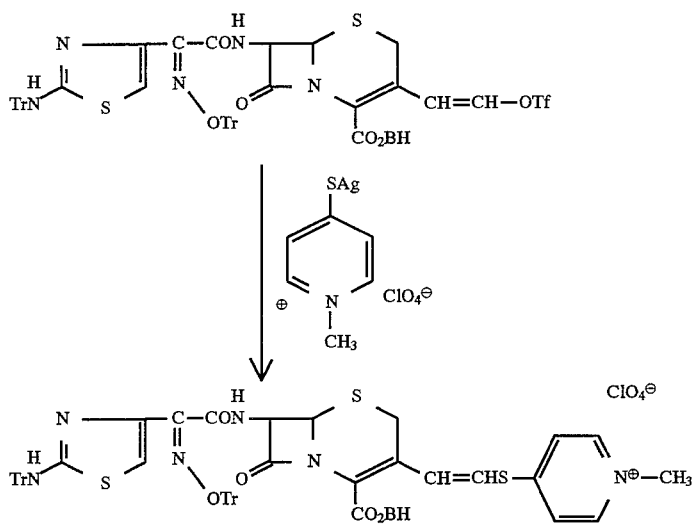

[wherein Tf represents a trifluoromethanesulfonyl group]

Benzhydryl 7-[2-trityloxyimino-2-(2-trityl-aminothiazol-4-yl)acetamido]-3-(2-trifluoromethanesulfonyloxyvinyl)-3-cephem-4-carboxylate (81 mg), silver-1-methyl-pyridinium-4-sulfide perchlorate (45 mg) and lithium chloride (14.5 mg) were stirred together in dimethyl sulfoxide (1 ml) at room temperature for 4 days. Ethyl acetate (80 ml) was then added, and the mixture was washed with water (80 ml) 3 times and dried. Thereafter, the solvent was distilled off under reduced pressure to provide benzhydryl 7-[2-trityloxyimino-2-(2-tritylaminothiazol-4-yl)acetamido]-3-[2-(1-methyl-4pyridinio)thiovinyl]-3-cephem-4-carboxylate perchlorate (45 mg). The $^1$H-NMR spectrum of this compound was in agreement with that of the compound obtained in Example 4.

4-triazolio-5-yl)thiovinyl]-3-cephem-4-carboxylate iodide, the procedure of Example 19 was otherwise followed to provide 7-[2-hydroxyimino-2-(2-aminothiazol-4-yl) acetamido]-3-[2-(1,4-dimethyl-1,2,4-triazolio-5-yl) thiovinyl]-3-cephem-4-carboxylate.

$^1$H-NMR (DMSO-d$_6$)δ ppm; 3.22 (1H, d, J=17.4 Hz), 3.24 (1H, d, J=17.4 Hz), 3.76 (1H, s), 4.03 (3H, s), 5.04 (1H, dr J=5.1 Hz), 5.61 (1H, dd, J=5.1, 8.1 Hz), 6.24 (1H, d, J=15.3 Hz), 6.63 (1H, s), 7.11 (2H, m), 7.43 (1H, d, J=15.3 Hz), 9.42 (1H, d, J=8.1Hz), 10.06 (1H, s), 11.32 (1H, s)

EXAMPLE 33

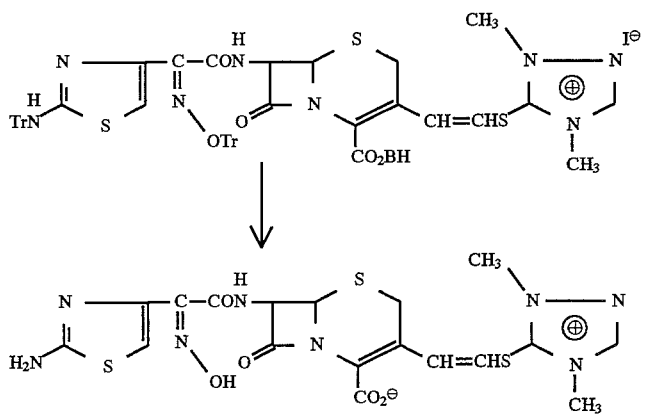

Using benzhydryl 7-[2-trityloxyimino-2-(2-tritylaminothiazol-4-yl)acetamido]-3-[2-(1,4-dimethyl1,2,

EXAMPLE 34

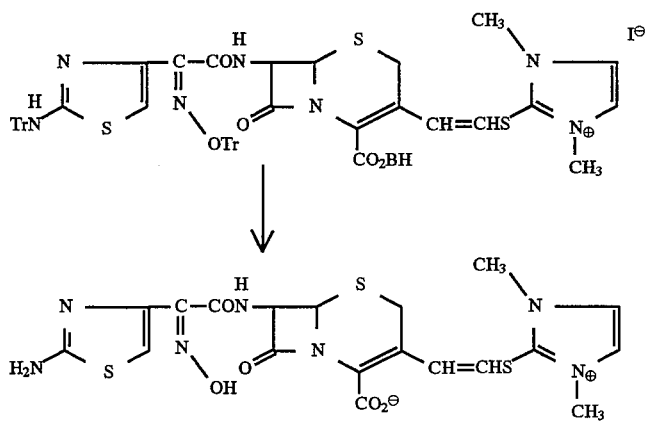

Using benzhydryl 7-[2-trityloxyimino-2-(2-tritylaminothiazol-4-yl)acetamido]-3-[2-(1,3-dimethylimidazolio-2-yl)thiovinyl]-3-cephem-4-carboxylate iodide, the procedure of Example 19 was otherwise followed to provide 7-[2-hydroxyimino-2-(2-aminothiazol-4-yl)acetamido]-3-[2-(1,3-dimethylimidazolio-2-yl)thiovinyl]-3-cephem-4-carboxylate.

$^1$H-NMR (DMSO-$d_6$)δ ppm; 3.36 (1H, d, J=17.4 Hz), 3.38 (1H, d, J=17.4 Hz), 3.85 (6H, s), 4.99 (1H, d, J=4.8 Hz), 5.58 (1H, dd, J=4.8, 8.1 Hz), 6.25 (1H, d, J=15.3 Hz), 6.62 (1H, s), 7.10 (2H, m), 7.30 (1H, d, J=15.3 Hz), 7.92 (2H, s), 9.38 (1H, d, J=8.1 Hz), 11.30 (1H, s)

the procedure of Example 19 was otherwise followed to provide 7-[2-hydroxyimino-2-(2-aminothiazol-4-yl)acetamido]-3-[2-(1,3-dimethyl-1,2,3-triazolio-5-yl)thiovinyl]-3-cephem-4-carboxylate.

$^1$H-NMR (DMSO-$d_6$)δ ppm; 3.40 (1H, d, J=17.4 Hz), 3.49 (1H, d, J=17.4 Hz), 4.18 (3H, s), 4.26 (3H, s), 5.02 (1H, d, J=5.1 Hz), 5.60 (1H, dd, J=5.1, 8.1 Hz), 6.21 (1H, d, J=15.3 Hz), 6.63 (1H, s), 7.10 (2H, m), 7.42 (1H, d, J=15.3 Hz), 9.05 (1H, s), 9.39 (1H, d, J=8.1 Hz), 11.30 (1H, s)

EXAMPLE 35

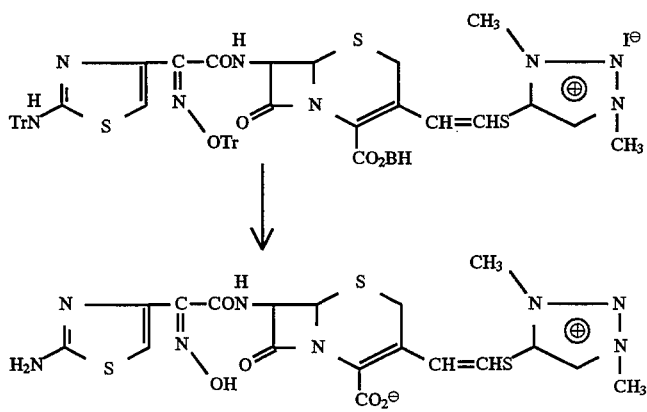

Using benzhydryl 7-[2-trityloxyimino-2-(2-tritylaminothiazol-4-yl)acetamido]-3-[2-(1,3-dimethyl1,2,3-triazolio-5-yl)thiovinyl]-3-cephem-4-carboxylate iodide,

EXAMPLE 36

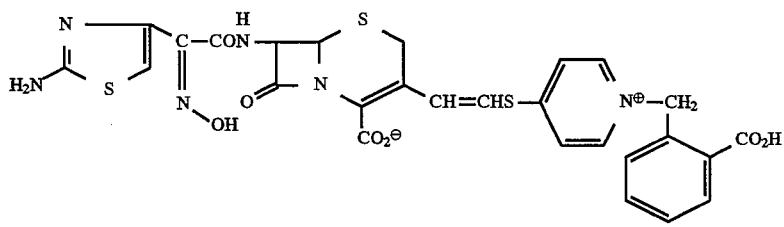

Using benzhydryl 7-[2-trityloxyimino-2-(2-tritylaminothiazol-4-yl)acetamido]-3-{2-[(1-(2-diphenyl-methoxycarbonylbenzyl)-4-pyridinio]thiovinyl}-3-cephem-4carboxylate iodide, the procedure of Example 19 was otherwise followed to provide 7-[2-hydroxyimino-2-(2-aminothiazol-4-yl)acetamido]-3-{2-[1-(2-carboxybenzyl)-4-pyridinio]thiovinyl]-3-cephem-4-carboxylate.

$^1$H-NMR (DMSO-d$_6$)δ ppm; 3.54 (1H, d, J=17.1 Hz), 3.77 (1H, d, J=17.1 Hz), 5.08 (1H, d, J=5.1 Hz), 5.67 (1H, dd, J=5.1, 8.1 Hz), 5.99 (2H, brs), 6.58 (1H, d, J=15.3 Hz), 6.64 (1H, s), 7.11 (2H, brs), 7.2–7.95 (4H, m), 7.42 (1H, d, J=15.3 Hz), 7.96 (2H, d, J=7.0 Hz), 8.78 (2H, d, J=7.0 Hz), 9.45 (1H, d, J=8.1 Hz)

We claim:

1. A cephem compound of the formula

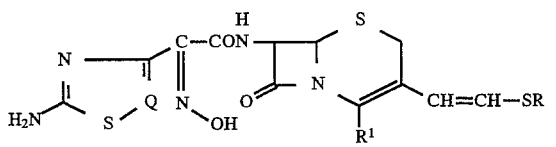

wherein Q represents CH;

R$^1$ represents a carboxylate or a carboxyl group; and

R represents the group

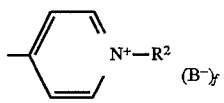

wherein R$^2$ represents a lower alkyl group, a loweralkenylgroup, a hydroxyloweralkyl group or the group —A—CO—R$^3$, wherein A represents a C$_{1-6}$ alkylene group; R$^3$ represents a hydroxyl group, a loweralkyl group, an amino group or a loweralkylamino group; B$^-$ represents an anion; and f is equal to 0 when R$^1$ represents a carboxylate groups and 1 when R$^1$ represents a carboxyl group; or a cephemcarboxy-protective ester thereof or a nontoxic salt thereof.

2. A compound according to claim 1 which is 7-[2-hydroxyimino-2-(2-aminothiazol-4-yl)acetamido]-3-[2-(1-carbamoylmethyl-4-pyridinio)thiovinyl]-3-cephem-4-carboxylate, 7-[2-hydroxyimino-2-(2-aminothiazol-4-yl) acetamido]-3-[2-(1-ethyl-4-pyridinio)thiovinyl]-3-cephem-4-carboxylate, 7-[2-hydroxyimino-2-(2-aminothiazol-4-yl) acetamido]-3-{2-[1-(2-hydroxyethyl)-4-pyridinio]thiovinyl}-3-cephem-4-carboxylate, 7-[2-hydroxyimino-2-(2-aminothiazol-4-yl)acetamido]-3-[2-(1-carboxymethyl-4-pyridinio)thiovinyl]-3-cephem-4-carboxylate, 7-[2-hydroxyimino-2-(2-aminothiazol-4-yl)acetamido]-3-[2-(1-acetonyl-4-pyridinio) thiovinyl]-3-cephem-4-carboxylate, 7-[2-hydroxyimino-2-(2-aminothiazol-4-yl)acetamido]-3-[2-(1-methyl-2-pyridinio)thiovinyl]-3-cephem-4-carboxylate, 7-[2-hydroxyimino-2-(2-aminothiazol-4-yl) acetamido]-3-{2-[1-(N,N-diethylamnocarbonylmehyl)-4-pyridinio)]thiovinyl}-3-cephem-4-carboxylate and 7-[2-hydroxyimino-2-(2-aminothiazol-4-yl]acetamido]-3-[2-(1-allyl-4-pyridinio)thiovinyl]-3-cephem-4-carboxylate; or a nontoxic salt thereof.

3. A pharmaceutical composition for the treatment of infectious diseases associated with merleillin-resist *Staphylococcus aureus* which comprises a cephera compound of the formula

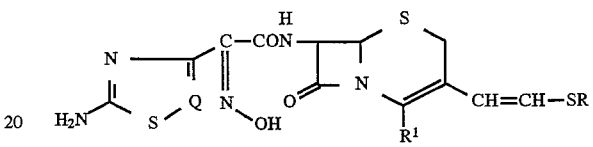

wherein Q represents CH;

R$^1$ represents a carboxylate group or a carboxyl group; and

R represents the group

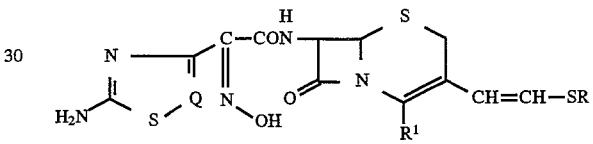

wherein R$^2$ represents a loweralkyl group, a loweralkenyl group, a loweralkynyl group, a hydroxylloweralkyl group or the group —A—CO—R$^3$, wherein A represents a C$_{1-6}$ alkylene group; R$^3$ represents a hydroxyl group, a loweralkyl group, an amino group, or a loweralkylamino group; B$^-$ represents an anion; and f is equal to 0 when R$^1$ represents a carboxylate groups and 1 when R$^1$ represents a carboxyl group; or a cephemcarboxy-protective ester thereof or a nontoxic salt thereof; and a pharmaceutically acceptable carrier.

4. The compound according to which claim 1 which is 7-[2-hydroxyimino-2-(2-aminothiazol-4-yl)acetamido]-3-[2-(1-methyl-4-pyridinio)thiovinyl]-3-cephem-4-carboxylate or a nontoxic salt thereof.

* * * * *